(12) United States Patent
Jennings et al.

(10) Patent No.: US 7,595,412 B2
(45) Date of Patent: Sep. 29, 2009

(54) POLYMER DISPERSIBLE POLYBASIC METAL CARBOXYLATE COMPLEXES

(75) Inventors: Thomas Jennings, Shaker Heights, OH (US); Ssatyan Kodali, Dover, OH (US); W. Matthew Fender, Dundee, OH (US); Donald R. Stevenson, Dover, OH (US)

(73) Assignee: Dover Chemical Corporation, Dover, OH (US)

( * ) Notice: Subject to any disclaimer, the term of this patent is extended or adjusted under 35 U.S.C. 154(b) by 655 days.

(21) Appl. No.: 10/486,769

(22) PCT Filed: Aug. 5, 2002

(86) PCT No.: PCT/US02/24724

§ 371 (c)(1),
(2), (4) Date: Feb. 12, 2004

(87) PCT Pub. No.: WO03/016395

PCT Pub. Date: Feb. 27, 2003

(65) Prior Publication Data

US 2004/0242908 A1     Dec. 2, 2004

(51) Int. Cl.
*C07C 59/147*    (2006.01)
*C07C 59/185*    (2006.01)
(52) U.S. Cl. .................. 554/121; 554/220; 554/221; 554/223; 562/887
(58) Field of Classification Search .......... 554/121, 554/220, 221, 223; 562/887
See application file for complete search history.

(56) References Cited

U.S. PATENT DOCUMENTS

| | | | |
|---|---|---|---|
| 4,200,544 A * | 4/1980 | Forsberg .................. | 508/391 |
| 4,369,276 A | 1/1983 | Wirth et al. .............. | 524/104 |
| 4,369,277 A | 1/1983 | Wirth et al. .............. | 524/104 |
| 4,385,147 A | 5/1983 | Wirth et al. .............. | 524/207 |
| 4,425,280 A | 1/1984 | Ho ........................... | 260/429 |

(Continued)

FOREIGN PATENT DOCUMENTS

EP          0 017 827          10/1980

(Continued)

OTHER PUBLICATIONS

Derwent Abstr. XP002224932, 1996.*

(Continued)

*Primary Examiner*—Deborah D Carr
(74) *Attorney, Agent, or Firm*—Louis F. Wagner; Hahn Loeser + Parks LLP

(57) ABSTRACT

A novel composition and methods of its use and preparation of polybasic metal carboxylate complexes having the general formula:

$$(A)_2 M \cdot n D(OH)_2 \cdot x H_2O \cdot m (B)_2 N$$

wherein: A is an organic fatty acid and is selected from the group consisting of saturated $C_{12-24}$ carboxylic acids, unsaturated $C_{12-24}$ carboxylic acids, aromatic $C_{12-24}$ carboxylic acids, alicyclic $C_{12-24}$ carboxylic acids, polycarboxylic acid derivatives thereof, anhydride derivatives thereof and blends thereof, preferably stearate; M is a divalent metal cation, preferably calcium; n is a fractional or whole number from about 1 to about 10 inclusive; D is an alkali earth metal, preferably calcium; x is a fractional or whole number from about 0 to about 3 inclusive; N is a divalent metal cation other than calcium, preferably zinc; and m is a fractional or whole number from 0 to about 1.

46 Claims, 12 Drawing Sheets

U.S. PATENT DOCUMENTS

| | | | | |
|---|---|---|---|---|
| 4,656,209 A | 4/1987 | Wehner et al. | ................. | 524/87 |
| 4,727,104 A | 2/1988 | Wehner et al. | ................. | 524/106 |
| 4,755,549 A | 7/1988 | Kemper et al. | ................. | 524/226 |
| 4,767,804 A | 8/1988 | Willoughby | ................. | 523/351 |
| 4,775,723 A | 10/1988 | Kuhne et al. | ................. | 525/327 |
| 4,927,548 A | 5/1990 | Hirsch et al. | | |
| 4,999,400 A | 3/1991 | Kuhne et al. | ................. | 525/196 |
| 5,124,373 A | 6/1992 | Baumgaertel et al. | ....... | 523/210 |
| 5,744,525 A | 4/1998 | Harvey et al. | ................. | 524/84 |
| 5,969,015 A | 10/1999 | Zinke et al. | ................. | 524/109 |
| 5,985,959 A | 11/1999 | Harvey et al. | ................. | 524/84 |
| 6,013,703 A | 1/2000 | Kuhn et al. | ................. | 524/100 |
| 6,348,164 B1 | 2/2002 | Khattar et al. | ............. | 252/404 |

FOREIGN PATENT DOCUMENTS

| | | | |
|---|---|---|---|
| EP | 0 330 097 | | 8/1989 |
| EP | 330097 | * | 8/1989 |
| EP | 0 330 097 | | 9/1989 |
| EP | 0 330 907 | | 9/1989 |
| RU | 1809600 | | 3/1996 |
| RU | 1809600 A1 | | 3/1996 |

OTHER PUBLICATIONS

S. Kodali, W. Hood, M. Fender; Highly Basic Calcium Stearate Compositions for Rigid PVC; ACS 222nd Nat'l Meeting; Aug. 2001.
D. Stevenson; Flame-Retardant Formulations for HIPS and olyolefins Using Chlorinated Paraffins; FRCA Meeting; Mar. 2002.
ACS 222$^{nd}$ National Meeting, S. Kodali, W. Hood, M. Fender, Aug. 2001, Highly Basic Calcium Stearate Compositions for Rigid PVC Applications.
FRCA Meeting, D. Stevenson, Mar. 2002, Flame-Retardant Formulations for HIPS and Polyolefins Using Chlorinated Paraffins.
PCT/US02/24724 Written Opinion dated Jul. 19, 2004.
Derwent Abstract; XP-002224932.

* cited by examiner

Effect of Zinc-modified Compositions

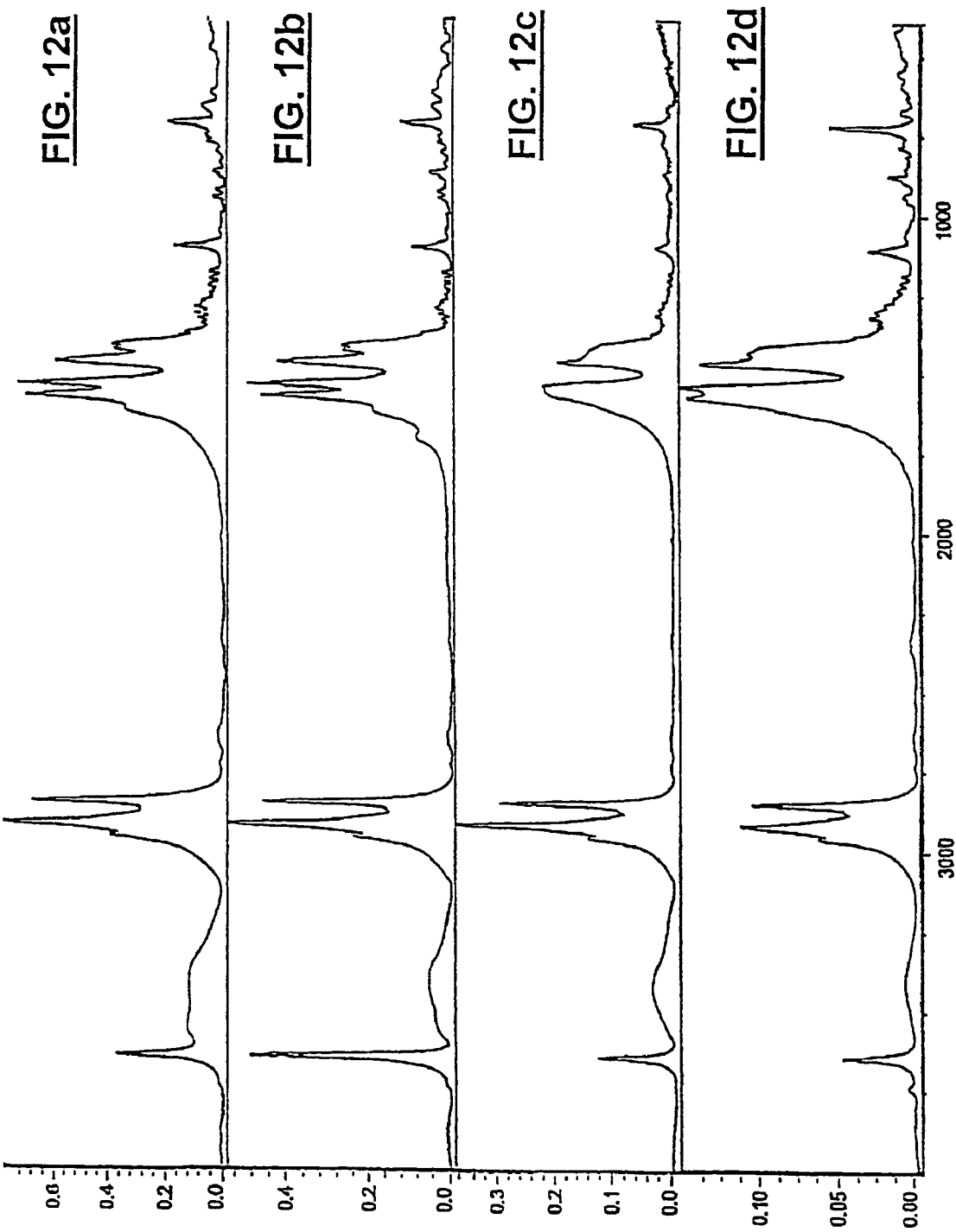

POLYMER DISPERSIBLE POLYBASIC METAL CARBOXYLATE COMPLEXES

BACKGROUND OF THE INVENTION

Calcium stearate is a multipurpose polymer additive and is widely used in the polymer industry as a lubricant, processing aid and stabilizer. The single biggest use is in conjunction with primary organotin mercaptide heat stabilizers in the extrusion of rigid PVC pipe, siding and profiles. Other significant uses are in polyolefins, phenolics, reinforced polyester and rubber.

Calcium stearate is as an internal lubricant and secondary heat stabilizer used in rigid PVC extrusion applications such as pipe, siding and profile where it is generally used at levels between 0.5 and 2.0 parts per hundred parts resin. Calcium stearate is thought to be effective at these low use levels because of a combination of properties including its polarity; its waxy character; its dispensability; its limited compatibility; and its melt viscosity at polymer processing temperatures. The effectiveness of calcium stearate is somewhat limited by its instability in the presence of strong acids, its tendency to plate out and its propensity to build up static charge and to form combustible dusts in air.

Without being held to any one theory of operation or mechanism, it is widely believed that calcium stearate functions as a secondary heat stabilizer in rigid PVC by reacting with and absorbing HCl generated as a result of heat degradation of the polymer during processing as illustrated in Equation 1.

$$(RCOO)_2Ca + 2HCl \rightarrow CaCl_2 + 2RCOOH \quad (1)$$

When calcium stearate is consumed in this manner its effectiveness as an internal lubricant is diminished.

Calcium stearate is supplied commercially as either a fine (sub 325 mesh) powder or a free flowing (20-100 mesh) granule. The granular product is the preferred form because of dust explosivity and plant hygienic issues associated with the handling of fine powders. Calcium stearate is usually formed by the reaction of stearic acid with calcium hydroxide (slaked lime) or calcium oxide (quick lime).

Calcium hydroxide and calcium oxide also find limited use as polymer additives. Calcium hydroxide is used as an acid neutralizer and calcium oxide is used primarily as a desiccant. Both materials are non-melting at polymer processing temperatures and as a result must be ground to extremely fine powders before the incorporation into polymer compounds. Both materials are highly polar and as a result are difficult to disperse in non-polar polymers with high melt viscosities. Calcium hydroxide and calcium oxide powders have a strong tendency to absorb $CO_2$ and moisture which give rise to poor handling properties, passivated surfaces and loss of effectiveness. Both present significant hygienic and plant housekeeping problems to the compounder.

A combination of economic and environmental issues have prompted rigid PVC formulations to continually strive to lower the use levels or completely replace primary heat stabilizers based upon organotin, barium, cadmium, and lead as well as compounding ingredients which are difficult to handle.

Both calcium stearate and calcium hydroxide function as secondary heat stabilizers for rigid PVC by absorbing HCl. There is a synergistic effect when calcium stearate and calcium hydroxide are used in combination. From a practical standpoint, however, the addition of both calcium stearate and calcium hydroxide separately represents an additional compounding step exacerbated by the additional handling problems associated with fine ground calcium hydroxide. Adding a single physical pre-blend of calcium stearate and calcium hydroxide also raises problems in that granules are the preferred form for calcium stearate because of dust explosivity concerns and fine ground powder is the required form for effectiveness of calcium hydroxide. Furthermore, the significant differences in particle size between granular calcium stearate (20 mesh) and fine ground calcium hydroxide (sub 325 mesh) coupled with the differences in specific gravity between calcium stearate (1.0) and calcium hydroxide (2.3) preclude the preparation of homogeneous non-segregating, storage stable blends of calcium stearate and calcium hydroxide. Melt blending of calcium stearate with any significant quantity of $Ca(OH)_2$ and subsequent grinding is not an option because calcium stearate decomposes at the melting point of $Ca(OH)_2$ and the melt viscosity of calcium stearate is too viscous to allow for the effective dispersion therein of any significant quantity of fine ground $Ca(OH)_2$. Polymer bound concentrates of calcium stearate and calcium hydroxide are not practical because of cost considerations.

It would therefore be desirable to have a heat stabilizer exhibiting desirable aspects of both calcium stearate and calcium hydroxide without the attendant physical handling and blending issues.

SUMMARY OF THE INVENTION

In one aspect, the present invention is directed to improving the performance of metal carboxylate secondary heat stabilizers.

Accordingly, one object of the present invention provides a metal carboxylate composition comprising the formula (2)

$$(RCOO)_2M.nM(OH)_2.xH_2O \quad (2)$$

wherein:

M is a divalent metal ion;

$RCOO^{\ominus}$ is a fatty carboxylate anion;

n is a fractional or whole number from about 1 to about 10 inclusive, and x is a fractional or whole number from about 0 to about 3 inclusive.

It is another object of the present invention to provide a method for making a metal carboxylate.

It is another object of the present invention to provide a method of stabilizing polymers.

Another object of this invention is the production of novel compositions of dispersed $Ca(OH)_2$ in a calcium stearate matrix.

Another object of this invention is to provide novel compositions of dispersed $Ca(OH)_2$ and zinc stearate in a calcium stearate matrix.

An additional object of the invention is to produce complexes of calcium stearate and $Ca(OH)_2$ which are resistant to stratification, demixing, the absorption of $CO_2$ complexes which are inherently buffered to prevent the decomposition of calcium stearate in acidic environments.

It is another object of this invention to produce basic calcium stearate complexes which improve the performance of calcium stearate in rigid PVC extrusion compounds stabilized with organotin or zinc primary heat stabilizers.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof, and wherein:

FIG. 12A is an FTIR spectrum of a powder calcium stearate composition having a molar excess of calcium hydroxide equivalent to n=3;

FIG. 12B is an FTIR spectrum of a powder sample of a physical blend of neutral calcium stearate and calcium hydroxide having a molar excess of calcium hydroxide equivalent to n=3;

FIG. 12C is an FTIR spectrum of a melt calcium stearate composition with calcium hydroxide having a molar excess of calcium hydroxide equivalent to n=3; and FIG. 12D is an FTIR spectrum of a melt physical blend of neutral calcium stearate and calcium hydroxide.

DETAILED DESCRIPTION OF THE INVENTION

Figure 1:
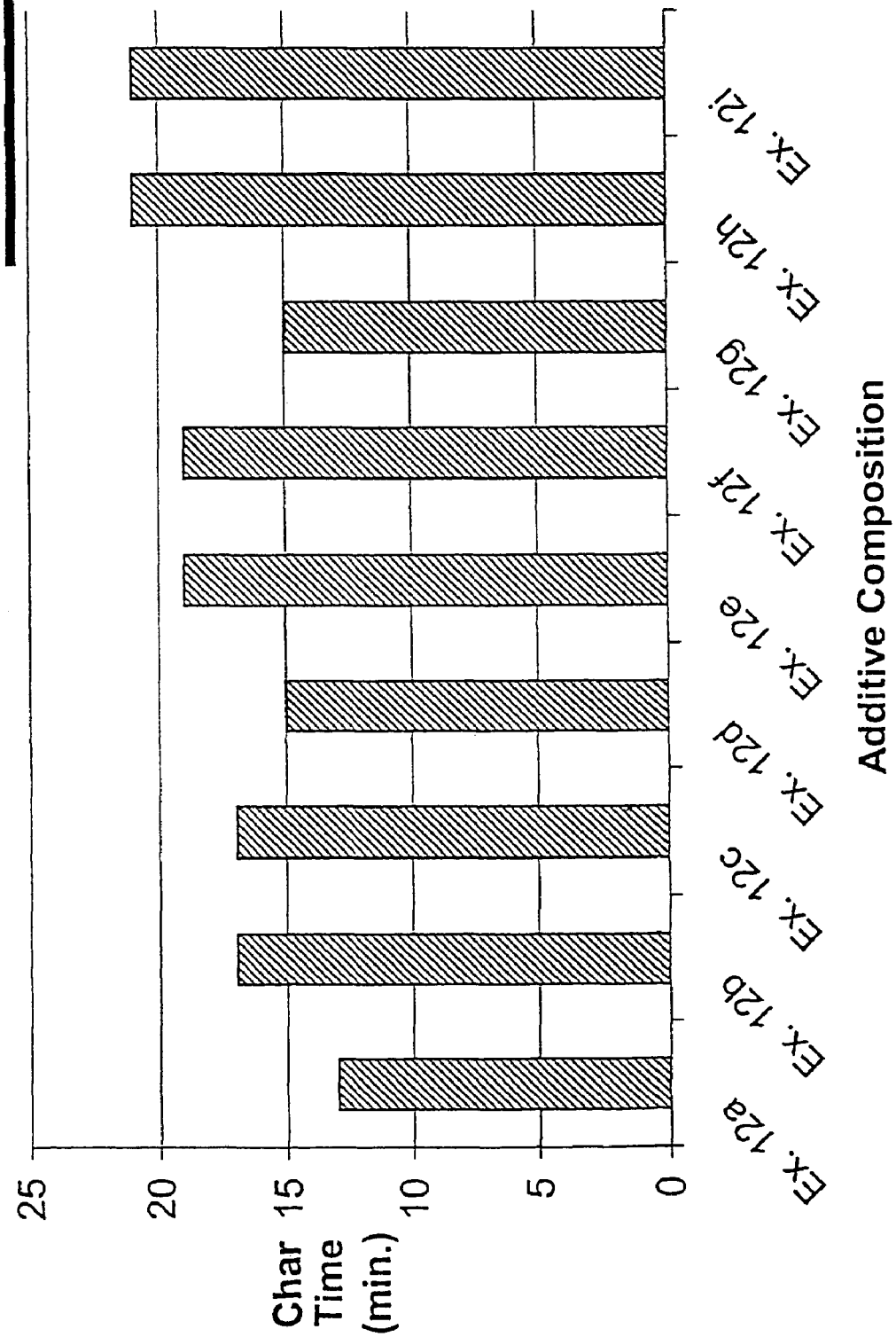
FIG. 1 is a dynamic Brabender testing sample sheet for organotin levels of 0.5, 0.75 and 1.0 phr organotin levels, with calcium and/or zinc stearate showing the processing window of the polymer.

In one specific embodiment, the compositions are solid complexes or dispersions with the empirical formula (3):

    (3)

where $RCOO^\ominus$ is a fatty carboxylate anion;
where n is >1; and
where x is 0 to 3 inclusive.

In another specific embodiment, the compositions are solid complexes or dispersions with the empirical formula (4):

    (4)

where $RCOO^\ominus$, n and x are as defined above, and m is 0 to 1 inclusive. These compositions can be characterized as polybasic soaps, interstitial complexes, or intimate solid dispersions.

The compositions rely for their effectiveness on the intimate dispersion of a "dispersed phase" (e.g. finely divided $Ca(OH)_2 \cdot H_2O$ and optionally, zinc stearate) in a continuous phase of calcium stearate.

The high melting point, high melt viscosity and decomposition temperature of calcium stearate preclude the intimate dispersion of significant quantities of $Ca(OH)_2 \cdot H_2O$ or zinc stearate by simple mechanical mixing of the ingredients into molten calcium stearate.

Accordingly, the compositions of the invention are prepared in a manner which takes advantage of the low melting point and low melt viscosity of stearic acid to essentially convert stearic acid into calcium stearate in the presence of the "to-be-dispersed phase" (e.g. $Ca(OH)_2 \cdot H_2O$ and optionally zinc stearate).

One advantage of this method is that the $Ca(OH)_2$ particles so dispersed are smaller, more nascent and protected against the adsorption of $CO_2$ and moisture and against stratification and demixing by virtue of being interdispersed, encapsulated or intercalated in a solid calcium stearate matrix.

It is desirable that the compositions be prepared at atmospheric pressure below the boiling point of water (e.g. 100° C.). If the compositions are prepared under pressure it is desirable that they be prepared below the glass transition temperature of calcium stearate (e.g. 120° C.). If these temperature conditions are not met the structure of the complexes may be disrupted by foam formation or by the collapse of the calcium stearate crystalline matrix.

One method of preparation of the complexes is under atmospheric conditions in batch or continuous mixers. Under these conditions heat is generated by the heat of formation of calcium stearate and any mechanical shear heating. This heat may be offset by either external cooling of the mixers or by internal heat sinks to ensure that the temperature of the reaction mass does not exceed 100° C. Carefully adjusted amounts of flake stearic acid, excess $Ca(OH)_2$, water or solid zinc stearate may serve as heat sinks to control temperature internally. Specific quantities to be added can be determined by trial and error or calculated from heats of formation and specific heats of the respective materials. The extent of complex formation can be indicated by the pH, hydrophobicity, particle size and resistance to demixing of the compositions.

Calcium stearate compositions when manufactured with excess lime in a prescribed fashion markedly improve the heat stability performance of calcium stearate in acidic polymeric environment such as PVC. The calcium stearate compositions further act in PVC to reduce plate out tendency and to reduce the propensity to accumulate static charge and form explosive mixtures in air. By use of the terms, "calcium hydroxide", "calcium oxide", and "calcium hydroxide or calcium oxide" in the current specification, it is to be understood that either of the materials or a combination of the two may be used in producing the present compositions.

In one embodiment, calcium carboxylate compositions of the present invention may be represented by the general formula (3).

    (3)

where the molar excess, n, is any fractional or whole number greater than 1 and up to 10, alternatively between about 2 and about 4, or alternatively about 3, $RCOO^\ominus$ is a fatty carboxylate anion such as the stearate ion $CH_3(CH_2)_{16}COO^\ominus$ and the like, and x is any fractional or whole number between 0 and about 3. By use of this general formula, the composition is not limited to a chemically bonded compound having the formula indicated. The composition may include an intimate mixture of calcium stearate, calcium hydroxide and water which is intimately mixed on a microscopic scale, with distinct regions of calcium stearate, water and calcium hydroxide incorporated into the composition. The composition may further include mixing of calcium stearate, calcium hydroxide, and water on a molecular level, with physical interaction of the calcium stearate, calcium hydroxide, and water moieties, or intercalation.

While some embodiments of the present invention are directed to calcium stearate compositions, the invention is not so limited. Metal carboxylate compositions of formula (1) are generally within the scope of the invention.

$$(RCOO)_2M.nM(OH)_2.xH_2O \tag{1}$$

where $(RCOO^{\ominus})$ is a fatty carboxylate, M is a divalent metal cation, n is any fractional or whole number from about 1 to about 10, and x is any whole or fractional number up to about 3. Alternatively, n may be from about 2 to about 4, and alternatively n may be about 3.

The methods and compositions of the present invention thus also include the use of metals other than calcium and metal hydroxides and oxides other than the calcium salts, including salts of divalent metals such as calcium, magnesium, lead, barium, strontium, zinc, iron, cadmium, nickel, copper, tin and mixtures of the above. Further, organic fatty acids other than stearic acid may be utilized, either singly or as mixtures. In one embodiment, the organic fatty acids may include $C_{12}$ to $C_{24}$ acids such as lauric (n-dodecanoic), myristic (n-tetradecanoic), palmitic (n-hexadecanoic), stearic (n-octadecanoic), arachidic (n-eicosanoic), behenic (n-docosanoic), and lignoceric (n-tetracosanoic), oleic, linoleic, and linolenic acids, and the like, or mixtures of these acids. Likewise, fatty acid carboxylate anions as given in formula (2) would correspondingly include the fatty carboxylates such as laurate, myristate, palmitate, stearate, etc. Commercial blends of fatty acids, generically described as "stearic acid", may be used. The commercial blends are generally blends of $C_{12}$ to $C_{24}$ fatty acids, with about 45 to 80 percent by weight of $C_{18}$ stearic acid, about 55 to 20 percent $C_{16}$ palmitic acid, and smaller amounts of other $C_{12}$ to $C_{24}$ fatty acids. Other organic fatty acids and their corresponding fatty carboxylates may also be used. The organic acid components used in the practice of this invention may include one or more organic acids that melt at temperatures above 20° C. or above 30° C. They include saturated and unsaturated aliphatic, aromatic, and alicyclic monocarboxylic, dicarboxylic, and polycarboxylic acids and the anhydrides of these acids. Examples of the useful acids include oleic acid, linoleic acid, linolenic acid, undecylenic acid, capric acid, melissic acid, monochloroacetic acid, trichloroacetic acid, chloroacrylic acid, hydroxystearic acid, oxalic acid, succinic acid, glutaric acid, adipic acid, azelaic acid, sebacic acid, brassidic acid, erucic acid, petroselic acid, maleic acid, fumaric acid, sorbic acid, citraconic acid, mesaconic acid, itaconic acid, glutaconic acid, malic acid, tartaric acid, citric acid, aconitic acid, tricarballylic acid, tetrolic acid, benzoic acid, m-chlorobenzoic acid, p-chlorobenzoic acid, 2,4-dichlorobenzoic acid, 2,3,6-trichlorobenzoic acid, 2,3,6-tribromobenzoic acid, 2,3,5,6-tetrachlorobenzoic acid, 2,3,5,6-tetrabromobenzoic acid, p-aminobenzoic acid, 3,4-dimethoxybenzoic acid, p-tert-butylbenzoic acid, 2,6-dinitrobenzoic acid, salicyclic acid, p-hydroxybenzoic acid, 2,4-dihydroxybenzoic acid, gallic acid, phenylacetic acid, cinnamic acid, phthalic acid, isophthalic acid, terephthalic acid, trimellitic acid, trimesic acid, cyclohexanecarboxylic acid, cyclopentanecarboxylic acid, cyclopentane-1,2-dicarboxylic acid, abietic acid, and the like. Illustrative of the acid anhydrides that can be used are maleic anhydride, succinic anhydride, glutaric anhydride, cinnamic anhyride, benzoic anhydride, phthalic anhydride, 3-nitrophthalic anhydride, and tetrachlorophthalic anhydride.

Compositions comprising one or more metals and one or more organic acids are also within the scope of this invention. For example, calcium stearate might be combined with zinc hydroxide, or zinc stearate with calcium hydroxide. As another example, a blend of various fatty acids of $C_{12}$ to $C_{24}$ may be used with one or more metal hydroxides or oxides. It will be apparent to one of ordinary skill in the art that a variety of combinations of the metal hydroxides or oxides, and organic fatty acids, is possible and resulting compositions may be produced using the methods of the present invention without undue experimentation.

The compositions of the present invention may be prepared by any mixing process wherein intensive mixing is experienced by the component stearic acid and calcium hydroxide or calcium oxide. Suitable mixing may be achieved using various suitable mixing equipment including horizontal plow mixers such as a Littleford mixer, Henschel Mixers, Waring blenders, or the like or with an extruder.

One aspect of the present invention is the preparation of calcium stearate compositions in situ by mixing stearic acid with between 100 percent and 1000 percent stoichiometric excesses of Ca $(OH)_2$ and catalytic quantities of water and subsequently allowing the mixtures to react at atmospheric pressure in a temperature range between ambient and the boiling point of water according to Equation 5.

$$2RCOOH + (n+1)Ca(OH)_2 \rightarrow (RCOO)_2Ca.nCa(OH)_2.2H_2O \tag{5}$$

The calcium stearate composition may be made by a suitable batch or continuous process wherein a mixture of stearic acid, lime and water are mixed such that the ingredients are intimately mixed and the temperature of the mixture is not allowed to exceed the boiling point of water.

In one embodiment, the mixing of fatty acid and metal hydroxide may be done in a two step procedure. In this embodiment, stearic acid or any other suitable fatty acid or combination of fatty acids may be mixed in dry form with a dry form of calcium hydroxide, calcium oxide or any other suitable divalent metal hydroxides or oxides or combination thereof to form a first, dry mixture. By dry form it is meant that the fatty acid, metal hydroxide, or metal oxide is in a generally powdered, flake, or otherwise particulate form and is substantially free flowing particulate form or may be made into a substantially free flowing particulate form using standard delumping or deagglomerating equipment. The first mixture generally comprises calcium hydroxide and water, and may contain added dry stearic acid such that the molar ratio of calcium to carboxylic acid is from about 2:2 to about 11:2, more preferably the molar ratio of metal to carboxylic acid is from about 3:2 to about 5:2, and most preferably, the molar ratio of metal to carboxylic acid is about 4:2. Alternatively, the first mixture comprises calcium hydroxide, water and no added dry stearic acid.

Water may be added to the first mixture before, during or after addition of the dry ingredients. Water is added in a catalytic amount to promote reaction of the fatty acid with the metal hydroxide or oxide. This amount of water may range from no added water to enough water to about 1.5 moles of water per mole of fatty acid. The amount of water added generally affects the reaction rate, with less water resulting in a slower reaction and more water resulting in a faster reaction. Water in excess of the catalytic amount may be added to control the temperature of the reaction through evaporative heat transfer. The first mixture is mixed in suitable mixing equipment for a sufficient time to ensure complete mixing of the dry ingredients and water. Generally, the dry fatty acid, metal hydroxide or metal oxide, and water are mixed for a time ranging from about 1 to about 10 minutes, as is needed to achieve adequate mixing with the particular mixing equipment being used. A longer mixing time may be required as will be apparent without undue experimentation.

After mixing of the first mixture, molten fatty acid is added to the first mixture with stirring in the mixing equipment. The molten fatty acid may be prepared by first melting the desired fatty acid or fatty acids in suitable heating apparatus, followed by transfer to the mixing equipment. The molten fatty acid is added to the first mixture to form a second mixture of the originally dry fatty acid, if any, the originally dry metal hydroxide or oxide, the water, and the molten fatty acid. The molten fatty acid is added to the first mixture over a time suitable with mixing to achieve uniform mixing in the second mixture. Generally, the molten fatty acid is added to the first mixture over a period of from about 5 minutes to about 15 minutes, as is needed to achieve adequate mixing. Further, the addition of the molten fatty acid promotes reaction of the fatty acid and metal hydroxide or oxide such that faster addition of the molten fatty acid results in a faster reaction, and slower addition results in a slower reaction. Mixing of the second mixture may be continued upon completion of the addition of the molten fatty acid for a period long enough to ensure complete reaction of the fatty acid and formation of the metal carboxylate compound. Generally, complete reaction of the fatty acid and formation of the metal carboxylate compound occurs with mixing of the second mixture for a time ranging from about 5 minutes to about 15 minutes. During the first and second mixing steps and the subsequent stirring of the second mixture, the mixtures exotherm due to the release of heat from the exothermic reaction of the fatty acid, metal hydroxide or oxide, and water. The mixture will generally exotherm to a temperature between ambient and the normal boiling point of water. By allowing the mixture to exotherm, it is meant that the mixture exhibits an increase in temperature due to the reaction wherein the temperature generally increases for a time, reaching a maximum temperature before cooling off.

The fatty acid may thus be added in two parts, a first part may be added in a dry form in the first mixture of the first mixing step, and a second part added in molten form in the second mixture of the second mixing step. The fraction of the total fatty acid added in the first and second steps may generally range from about 0 percent to about 90 percent of the total added fatty acid being added in the dry form in the first mixture in the first mixing step, and from about 100 percent to about 10 percent of the total added fatty acid being added in the molten form in the second mixture in the second mixing step. In one embodiment, about 50 percent of the fatty acid is added in the dry form in the first mixture, and about 50 percent of the fatty acid is added in the molten form in the second mixture. The relative amounts of fatty acid added in the first and second mixtures will generally affect the rate at which the ingredients react to form the metal carboxylate composition. More molten fatty acid generally results in a faster reaction, and less molten fatty acid generally results in a slower reaction. In another embodiment, no dry fatty acid is added in the first mixture, and 100 percent of the fatty acid is added in the molten form into the second mixture.

Excess heat generated in the reaction of calcium hydroxide and stearic acid may further be removed through the use of external heat transfer media. External jackets or coils or the like with cooling water or heat transfer oil may be used as would be apparent to one skilled in the art.

In one embodiment, the calcium stearate composition may be modified with zinc stearate. Zinc stearate may be added in dry form to the first mixture such that the molar ratio of said zinc stearate to said fatty carboxylic acid is up to about 0.5, more preferably adding zinc stearate such that the molar ratio of said zinc stearate to said fatty carboxylic acid is about 0.125. In this embodiment, zinc stearate may be incorporated into the calcium stearate composition along with the excess calcium hydroxide. The compositions in this embodiment are solid complexes with the empirical formula (6)

$$(RCOO)_2Ca.nCa(OH)_2.xH_2O.m(RCOO)_2Zn \qquad (6)$$

where $RCOO^{\ominus}$, n and x are as defined above, and m is 0 to 1 inclusive, typically 0.25.

The material used in the evaluations was made using a Littleford unit. The process is similar to that of non-zinc modified compositions but with the addition of zinc stearate. The preparation of zinc modified calcium stearate can be done either by adding the finished zinc stearate when the lime is charged or after the reaction of the calcium stearate composition. In one embodiment, the method comprises the following steps in a Littleford mixer or the like: 1) charge the $Ca(OH)_2$; 2) charge the zinc stearate (15% by weight of total batch charge); 3) charge water; and 4) charge the liquid feed stearic acid with high intensity mixing. Total batch time may be approximately 30 minutes from start to finish. Reaction time may be 15-20 minutes.

The reaction does readily still occur if flake stearic acid is used as may be done in non zinc modified compositions of n=0 or n=0.3. The total stearic acid charge may be split 2:1. In one embodiment, the following procedure may be used: 1) charge $Ca(OH)_2$; 2) charge ⅔ total acid charge as solid flaked acid; 3) charge $H_2O$; and 4) mix the remaining ⅓ acid (in liquid form at approximately 87.8° C.) is slowly charged under high intense mixing in a Littleford mixer. The reaction is similar to the above system where the material will exotherm in slight excess of 100° C. where most of the water is released. The material is held at this temperature for only a couple minutes and cooling water is applied to the external jacket of the mixer. Material is discharged at <80° C.

Previous methods used to produce so-called overbased metal compositions require treatment of a metal hydroxide or oxide and fatty acid mixture with an acidic gas such as carbon dioxide. Typical prior art preparation of overbased metal compositions is taught for example in U.S. Pat. No. 3,147,232 wherein carbonation treatment with $CO_2$ is required to prepare a high metal ratio composition. By contrast, the present invention does not require treatment with $CO_2$ gas and the resulting product is therefore not carbonated.

The compositions of the invention can subsequently be cooled, crushed and sized to 20-100 mesh granules or ground to produce powders. When produced according to the method herein described the compositions are homogeneous, free flowing, non-segregating, storage stable, friable and readily polymer dispersible.

The metal carboxylates are suitable as heat stabilizers in halogenated polymers, including polyvinyl chloride (PVC), polyvinylidene chloride, chlorinated polyvinyl chloride (CPVC), chlorinated polyolefins, and the like. In one embodiment, the calcium stearate compositions of the present invention are suitable as secondary heat stabilizers in rigid PVC compounds as direct replacements for calcium stearate.

The compositions may also be used as secondary stabilizers used in combination with primary heat stabilizers based upon organotin or zinc compounds. The compositions may be used as polymer additives in combination with primary heat stabilizers based upon tin, zinc, hindered phenolic antioxidants or phosphites. The compositions may be used in combination with zinc carboxylates as heat stabilizers for rigid PVC compounds.

These compositions are superior to calcium stearate and blends of calcium stearate with $Ca(OH)_2$ or CaO as secondary heat stabilizers for rigid PVC compounds. The compositions of the invention contain none of the shortcomings associated with physical blends of calcium stearate with $Ca(OH)_2$ or CaO.

The compositions may be used in an effective amount as a heat stabilizer in halogenated resins; accordingly, the present invention includes in one aspect a halogenated resin composition containing an effective amount of the compositions of the present invention as a heat stabilizer. In one embodiment an effective amount may be in a range of about 0.5 to about 2 parts per hundred parts resin. The halogenated resin may include PVC. Further, a PVC resin composition containing an effective amount of a composition of the present invention as a secondary heat stabilizer in combination with a primary organotin stabilizer is included within the scope of the invention. The organotin stabilizer may be a methyl, butyl or octyl tin alkylthioglycolate or mercaptoethyl carboxylate.

A PVC resin composition containing an effective amount of a composition of the present invention as a secondary heat stabilizer in combination with a primary zinc stabilizer is included within the scope of the invention. The primary zinc stabilizer may be zinc stearate.

A PVC resin stabilizer composition containing a composition of the present invention may also include in combination with an organotin mercaptide or a zinc carboxylate. The zinc carboxylate may be zinc stearate.

A resin stabilizer composition may include an effective amount of a composition of the present invention in combination with a material selected from a group consisting of a phenolic antioxidant, a phosphite ester, or a zinc carboxylate.

The invention is further illustrated by the following non-limiting examples. These examples are presented for aiding in carrying out the invention and are described for the purposes of illustrating the best mode known to the applicant at the time. The examples are illustrative only and not meant to limit the invention, as measured by the scope and spirit of the claims.

EXAMPLE 1

(Monobasic Calcium Stearate) $(RCOO)_2 Ca.Ca(OH)_2.2H_2O$ 12.5 Kg of stearic acid flake and 6.6 Kg of $Ca(OH)_2$ were charged to a 100 L plough mixer, followed by mixing for 5 minutes. To the mixture were added 0.9 Kg of $H_2O$ with continuous mixing while adding 12.5 Kg of molten stearic acid. Mixing was continued for 10 minutes at atmospheric pressure. The batch exothermed to 99° C. The batch was then discharged, cooled, crushed and ground.

Analysis: % ash (As CaO)=15
% Free Fatty Acid=0.5
% Moisture=4.8

EXAMPLE 2

(Tribasic Calcium Stearate) $(RCOO)_2 Ca.3Ca(OH)_2.2H_2O$ 12.5 Kg of stearic acid flake and 13.6 Kg of $Ca(OH)_2$ was charged to a 100 L plough mixer, followed by mixing for 5 minutes. To the mixture was added 0.9 Kg of $H_2O$ with continuous mixing while adding 12.5 Kg of molten stearic acid. Mixing was continued for 10 minutes at atmospheric pressure. The batch exothermed to 93° C. The batch was then discharged, cooled, crushed and ground.

Analysis: % Ash (As CaO)=36
% Free Fatty Acid=0.2
% Moisture=4.0

EXAMPLE 3

(decabasic Calcium Stearate) $(RCOO)_2 Ca.10Ca(OH)_2.2H_2O$ 24.9 Kg of flake stearic acid, and 37.2 Kg of $Ca(OH)_2$ were charged to a 100 L ribbon blender. After start of blending, 2.3 Kg of water was added, followed by blending for 5 minutes. The batch was fed continuously to a 1 inch twin screw compounding extruder at 100 rpm. The extrudate temperature was 82° C. The extrudate was ground to a powder.

Analysis: % Ash (As CaO)=44
% Free Fatty Acid=0.1
% Moisture=3.5

EXAMPLE 4

Table 1 compares the performance of Examples 1-3 to calcium stearate, $Ca(OH)_2$, CaO and to blends of the same in dynamic Brabender heat stability tests. The table illustrates the superiority of the Examples to calcium stearate and simple mixtures of calcium stearate, $Ca(OH)_2$, CaO.

TABLE 1

Dynamic Heat Stability Results

| PHR | Test Material | Minutes to Decomposition |
|---|---|---|
| 0 | No additive | 15 |
| 1.5 | CaO | 16 |
| 1.5 | $Ca(OH)_2$ | 22 |
| 1.5 | $CaSt_2$ | 29 |
| 1.5 | $CaSt_2/CaO$ (1/1) Wt. (blend) | 21 |
| 1.5 | $CaSt_2/Ca(OH)_2$ (1/1) Wt. (blend) | 34 |
| 1.5 | Ex #1 $CaSt_2.Ca(OH)_2.2 H_2O$ | 38 |
| 1.5 | Ex #2 $CaSt_2.3 Ca(OH)_2.2 H_2O$ | 45 |
| 1.0 | Ex #2 $CaSt_2.3 Ca(OH)_2.2 H_2O$ | 35 |
| 0.75 | Ex #2 $CaSt_2.3 Ca(OH)_2.2 H_2O$ | 27 |
| 1.5 | Ex #3 $CaSt_2.10 Ca(OH)_2.2 H_2O$ | 42 |

| Base Formulation | Test Conditions |
|---|---|
| 100 PVC Resin | 180° C. |
| 1 $TiO_2$ | 45 rpm |
| 1 K120N | |
| 1 Paraffin Wax | |
| 1 Tin Stabilizer TM181 | |

Based on the homogeneity, the particle size, and the resistance to moisture and $CO_2$ absorption of the compositions of Examples 1-3, these compositions may consist of complex basic salts of $Ca(OH)_2$ encapsulated calcium stearate, or mixtures of various complexes of both components.

Based on the extended dynamic heat stability of Examples 1 to 3 when compared to calcium stearate, the compositions of the invention may regenerate any calcium stearate which is consumed by HCl. This regeneration process may be facilitated in some manner by the homogeneous structure of the present invention.

EXAMPLE 5

Neutral $CaSt_2$ (n=0)

275 g (1.0 mole) of flaked stearic acid, 74 g (1.0 mole) of $Ca(OH)_2$ and 10 g of water were mixed at ambient temperature in a horizontal plow mixer. Subsequently 275 g (1.0 mole) of melted stearic acid (at 75° C.) was added over 5 minutes. Mixing was continued for 10 minutes. Reactants exothermed to 100° C. Material was discharged and ground to a powder.

Analysis % Ash (CaO)=9.2
% Free Fatty Acid=<1
% $H_2O$=3.2

EXAMPLE 6

$CaSt_2.Ca(OH)_2.H_2O$ (n=1)

275 g (1.0 moles) of flaked stearic acid, 148 g (2.0 moles) of $Ca(OH)_2$ and 20 g of water were mixed at ambient temperature in a horizontal plow mixer. Subsequently 275 g (1 mole) of melted stearic acid (at 75° C.) was added over 5 minutes. Mixing was continued for 10 minutes. Reactants exothermed to 100° C. Material was discharged and ground to a fine powder.

Analysis % Ash (CaO)=16
% Free Fatty Acid=<1
% $H_2O$=2.8

EXAMPLE 7

Same as Example 2 using 4 moles of $Ca(OH)_2$ (n=3)

Analysis % Ash (CaO)=26.5
% Free Fatty Acid=<1
% $H_2O$=3.5

EXAMPLE 8

Same as Example 2 using 5 moles of $Ca(OH)_2$ (n=4)

Analysis % Ash (CaO)=31
% Free Fatty Acid=<1
% $H_2O$=3.4

EXAMPLE 9

Dry Blend (n=3)

1 g mole of calcium stearate monohydrate and 3 g mole of calcium hydroxide were combined in a container and vigorously shaken by hand to prepare a dry blend. No heat or other mixing means were used.

Analysis % Ash (CaO)=26.5
% Free Fatty Acid=<1
% $H_2O$=3.5

EXAMPLE 10

Examples 5-9 were evaluated in a rigid PVC formula for Brabender fusion time (lubricity), heat stability, and plate out resistance. The examples were also evaluated for explosivity index and static charge dissipation. The following procedures were used.

For the heat stability test, the formulated sample was fed in a Brabender PL2000 Plasticorder at 180° C. at 40 rpm screw speed. Every 5 minutes a sample was taken, and changes in color between successive samples were compared. The heat stability time was determined as the time in minutes when the change in sample color was considered to be significant.

For the fusion test, the sample was fed into a Brabender PL2000 Plasticorder at 180° C. The increase in torque, due to degradation and crosslinking is measured by the instrument. The time to reach this point is called fusion time. The longer the fusion time, the more stable is the given formulation.

For the plate out test, a sample doped with red dye was run on a two roll mill at 175° C. to 180° C. for 5 minutes. The rolls were then cleaned and residual color on the roll is indicative of plate out. Lack of color is indicative of no plate out and good lubricity. The base composition and test results are given in Table 2.

TABLE 2

| Additive | n | Heat Stability Minutes | Fusion Time minutes | Plate out |
|---|---|---|---|---|
| No additive | — | 10 | >10 | none |
| Ex #5 ($CaSt_2$) | 0 | 17 | 3 | Slight |
| Ex #6 ($CaSt_2.Ca(OH)_2.H_2O$) | 1 | 20 | 4 | None |
| Ex #7 ($CaSt_2.3\ Ca(OH)_2.H_2O$) | 3 | 26 | 3 | None |
| Ex #8 ($CaSt_2.4\ Ca(OH)_2.H_2O$) | 4 | 20 | 5 | None |
| Ex #9 ($CaSt_2.H_2O/3\ Ca(OH)_2$) (Dry Blend) | 3 | 15 | — | — |

| Base composition | |
|---|---|
| Parts | Component |
| 100 | PVC |
| 1 | $TiO_2$ |
| 2 | Acrylic IPM |
| 1 | Paraffin Wax |
| 1 | Organotin stabilizer |

EXAMPLE 11

Separation Visualization Test

The compositions of the present invention may further be distinguished from simple powdered blends of calcium stearate with $Ca(OH)_2$ or CaO. Generally, physical blends of calcium stearate with $Ca(OH)_2$ or CaO are not intimately mixed, and therefore easily separate. In contrast, the compositions of the present invention are an intimate mixture consisting of complex basic salts, $Ca(OH)_2$ encapsulated calcium stearate, or some mixture or complex of both. One illustration of the complex nature of the compositions of the present invention as compared with simple blends of calcium stearate with $Ca(OH)_2$ or CaO is illustrated by preparing four samples of calcium stearate compositions in water are shown. Sample A was a neutral calcium stearate, sample B was a tribasic calcium stearate of the present invention, sample C was $Ca(OH)_2$, and sample D was a simple blend of calcium stearate and $Ca(OH)_2$. Each of the samples was shaken with water and allowed to settle. In sample A, neutral calcium stearate floated on the water upon separation. In sample C, $Ca(OH)_2$ settled to the bottom upon separation. A comparison of samples B and D illustrated at least one significant difference between the compositions of the present invention and simple blends. In sample B, the calcium stearate composition floated on the water with no separation of $Ca(OH)_2$, suggesting that the $Ca(OH)_2$ is encapsulated or otherwise inseparably associated with the calcium stearate. By contrast, in sample D the Ca(OH)$_2$ was seen to settle to the bottom while the calcium stearate floated on top.

EXAMPLE 12

Dynamic Brabender Testing

Figure 2:
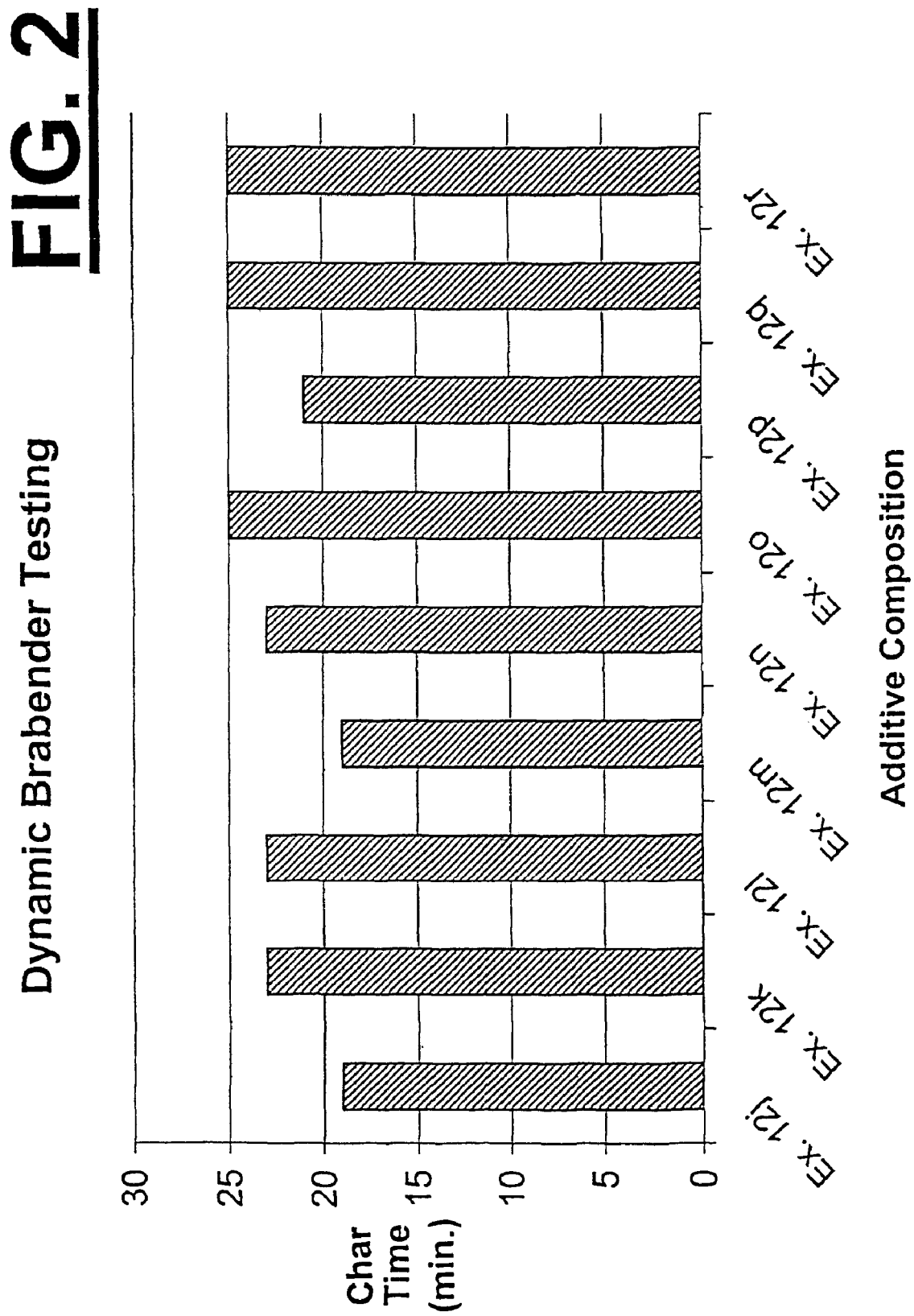
FIG. 2 is a dynamic Brabender testing sample sheet for organotin levels of 1.25, 1.50 and 1.75 phr organotin levels, with calcium and/or zinc stearate showing the processing window of the polymer.

Table 3 demonstrates the dynamic Brabender testing of various samples using the Brabender bowl mixer where polymer torque rheometry characteristics were measured. Samples consisting of 60 grams were evaluated at 60 rpm and 190° C. where samples were pulled at two-minute intervals after fusion. Each of the calcium stearate or calcium stearate/zinc stearate blends in having n=0.3 or 3, were evaluated at a constant organotin level, followed by evaluations at organotin levels increasing by increments of 0.25 phr, as shown in FIGS. 1 and 2.

TABLE 3

| Sample | | | | Fusion time | Time until charring | Color Stability |
|---|---|---|---|---|---|---|
| Ex # | Sn | Stearate | n | (sec) | (min) | YI |
| 12a | 0.5 | Ca | 0.3 | 68 | 13 | 27 |
| 12b | 0.5 | Ca | 3.0 | 62 | 17 | 27 |
| 12c | 0.5 | Ca/Zn | 3.0 | 76 | 17 | 12 |
| 12d | 0.75 | Ca | 0.3 | 58 | 15 | 23 |
| 12e | 0.75 | Ca | 3.0 | 56 | 19 | 23 |
| 12f | 0.75 | Ca/Zn | 3.0 | 64 | 19 | 11 |
| 12g | 1.0 | Ca | 0.3 | 62 | 15 | 19 |
| 12h | 1.0 | Ca | 3.0 | 46 | 21 | 19 |
| 12i | 1.0 | Ca/Zn | 3.0 | 56 | 21 | 10 |
| 12j | 1.25 | Ca | 0.3 | 52 | 19 | 16 |
| 12k | 1.25 | Ca | 3.0 | 56 | 23 | 16 |
| 12l | 1.25 | Ca/Zn | 3.0 | 68 | 23 | 11 |
| 12m | 1.5 | Ca | 0.3 | 52 | 19 | 15 |
| 12n | 1.5 | Ca | 3.0 | 60 | 23 | 15 |
| 12o | 1.5 | Ca/Zn | 3.0 | 62 | 25 | 9 |
| 12p | 1.75 | Ca | 0.3 | 42 | 21 | 13 |
| 12q | 1.75 | Ca | 3.0 | 54 | 25 | 13 |
| 12r | 1.75 | Ca/Zn | 3.0 | 48 | 25 | 8 |

| Base Formulation | |
|---|---|
| Parts | Component |
| 100 | PVC |
| 1 | TiO$_2$ |
| 1 | Acrylic Process Aid |
| 1 | Paraffin Wax |
| 0.5 to 1.75 | Organotin stabilizer |
| 1.0 | Calcium stearate or calcium stearate/zinc stearate blend, n = 0.3 or 3 |

FIG. 1 shows dynamic Brabender testing sample sheet for organotin levels of 0.5, 0.75, and 1.0 phr with calcium stearate and/or calcium stearate/zinc stearate blend while FIG. 2 shows Dynamic Brabender Testing sample sheet for organotin levels of 1.25, 1.50, and 1.75. This data shows how effective highly basic stearates can be. In nearly all cases, a 25% increase in long term stability was observed when high ash calcium stearate and/or calcium stearate/zinc stearate blends were used. For example, in FIG. 1, with organotin levels as low as 0.5 phr, the standard product (Ex. 12a) offers a very narrow processing window whereas in the same formulation with increased amounts of hydroxide, the processing window can easily be increased before polymer degradation occurs. In most rigid PVC applications, color retention is a major issue. It is seen from FIG. 3, that high ash calcium stearates can produce equal or better color retention. The early color hold and long-term heat stability are also superior.

EXAMPLE 13

Color Stability Data

Figure 3:
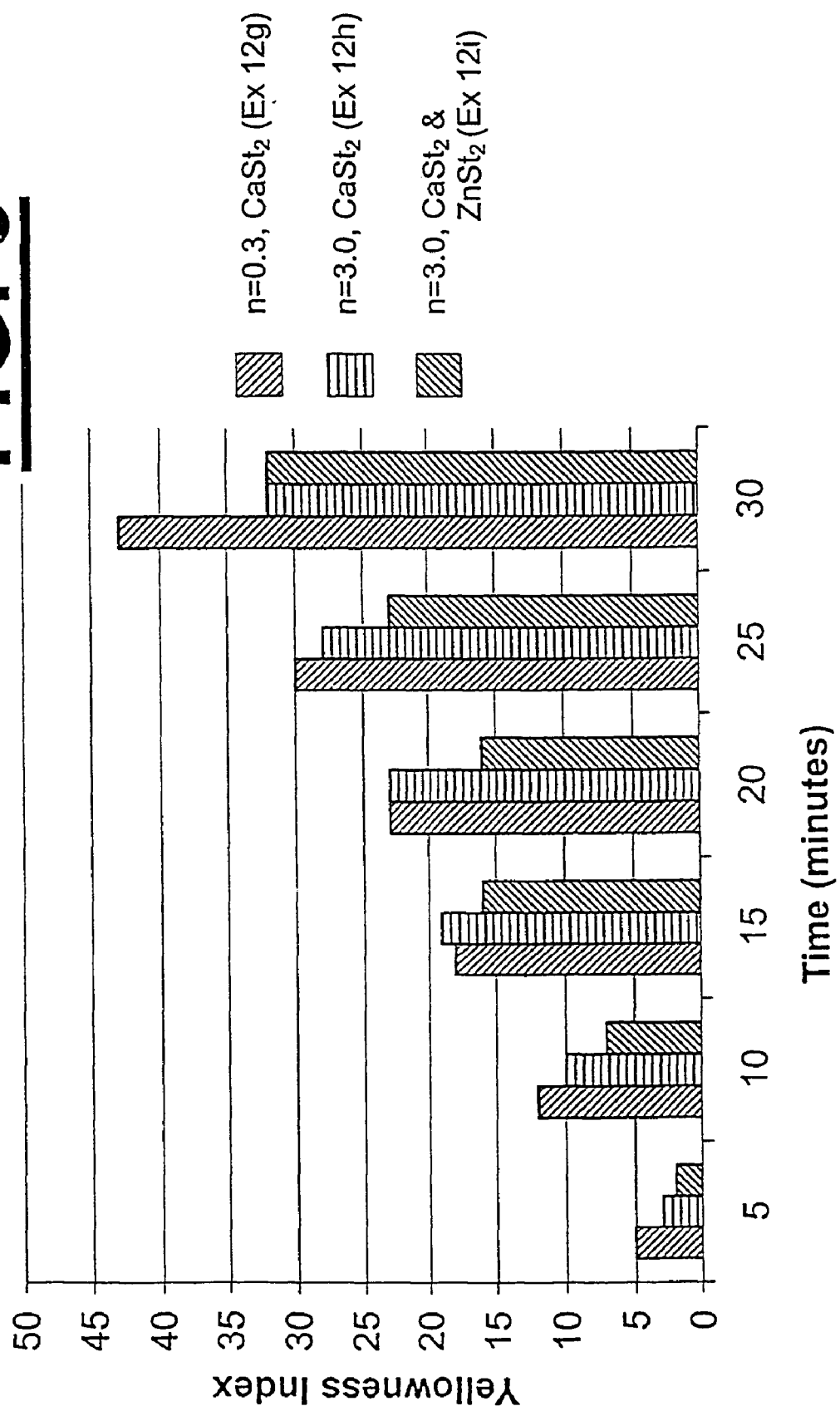
FIG. 3 is a graph of Yellowness Index over time to show relative rates of thermal degradation at a constant organotin stabilizer level.

Samples 12g, 12h and 12i in Table 3 were compounded in the Brabender bowl mixer at 60 rpm and 180° C. Samples were taken at five minute intervals and the Yellowness Index was measured to show relative rates of thermal degradation at a constant organotin stabilizer level. Results are shown in FIG. 3 and indicate the general trend in color retention when replacing the standard calcium stearate with a high ash product. This trend is reproducible at nearly any organotin loading level. The yellow index remains low and the L value, or whiteness, remains higher with the more basic stearates. In other words, the time at which thermal decomposition occurs is extended in every case when compared to standard products.

EXAMPLE 14

QUV Weathering Data

Figure 4:
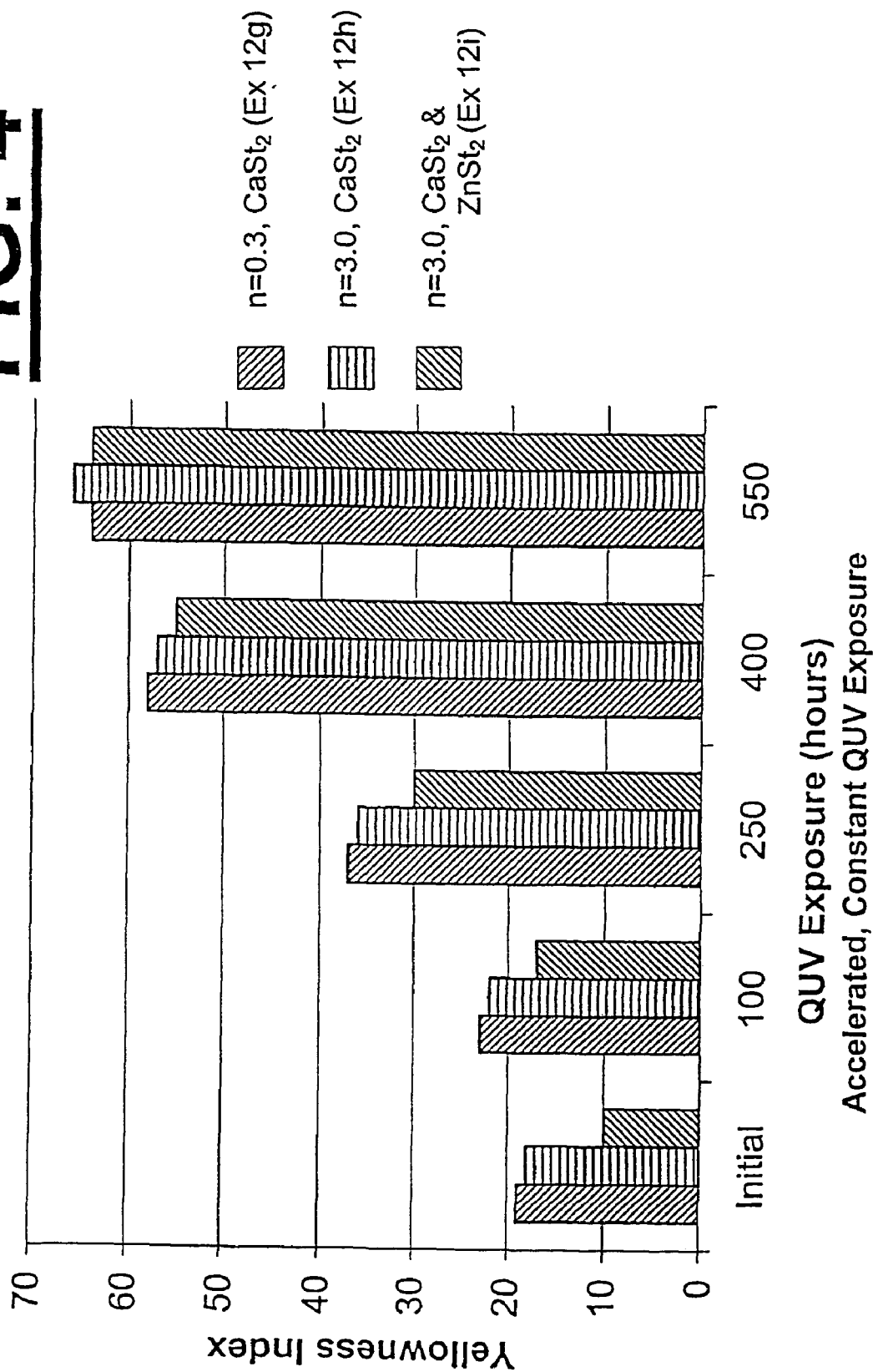
FIG. 4 is a graph of Yellowness Index over time to show relative rates of degradation of samples exposed to constant UV light in a weatherometer chamber.

Samples 12g, 12h and 12i in Table 3 were compounded on the roll mill at 190° C. for 5 minutes and 3"×3" plaques were pressed. Initial yellowness index colors were recorded and the samples were exposed to constant UV light in the weatherometer chamber. The samples were removed and YI was again measured at various time frames. Results are shown in FIG. 4 and illustrate that initial color and colors after accelerated QUV exposures are also better for the highly basic grades of calcium stearate.

EXAMPLE 15

Static Oven Testing Data

Figure 5:
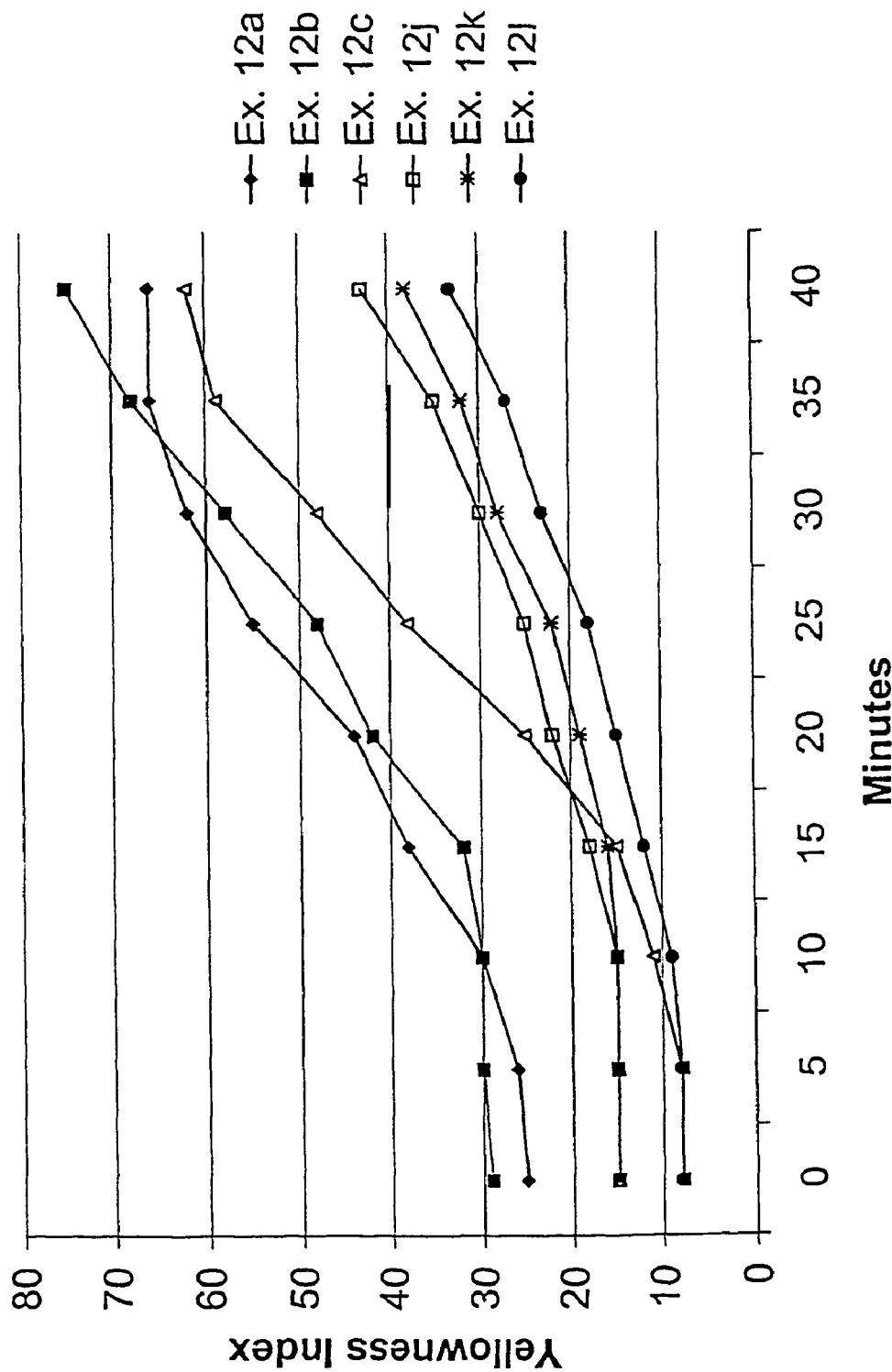
FIG. 5 is a graph of Yellowness Index over time to show relative rates of degradation of samples exposed to static heat of 190° C.

Samples in Table 3, at various tin stabilizer levels, were compounded on the roll mill at 190° C. for 4 minutes, cut into ½" strips, and placed in a Mathis Oven for standard 17 mm/5 minute intervals at 190° C. Yellowness index colors were then measured and plotted. Results are shown in FIG. 5 and illustrate that samples compounded with highly basic calcium stearates had markedly better color retention when exposed to intense static heat. Note that Example 12c (FIG. 5) at 0.5 phr organotin has lower YI than Example 12j at 1.25 phr organotin within the processing window.

EXAMPLE 16

Samples as given in Table 3 and prepared as in Example 15 were tested for various physical properties. Notched Izod was performed following ASTM D256; Heat deflection was performed following ASTM 648; and Tensile properties were tested following ASTM D638. Results are shown in Table 4.

TABLE 4

| Physical Property Evaluations of Rigid PVC | | | | |
|---|---|---|---|---|
| n, molar excess of Ca(OH)$_2$ | 0[b] | 0.3 | 3 | 3[c] |
| Notched Izod Ft Lbs./In. | 0.8 | 0.8 | 0.9 | 0.9 |
| Tensile Strength, PSI[a] | 8500 | 8500 | 8700 | 8800 |
| Tensile Ultimate % Elongation | 30 | 30 | 30 | 30 |

[a]Tensile test was run at 2.0 in./min.
[b]Control: Neutral Calcium Stearate
[c]Modified with 15% zinc stearate in calcium stearate composition

EXAMPLE 17

Incorporation of Excess $Ca(OH)_2$ into Calcium Stearate Composition

Samples of calcium stearate compositions were prepared using the methods of the present invention to have n=0, n=0.3, and n=3. Samples of each composition in water were prepared by adding the 10 g of the composition in 100 g of water followed by manual shaking. After shaking a portion of the water phase was pipetted out and pH of the water sample measured. The results are shown in Table 5 along for the calcium stearate compositions of the present invention, along with calcium hydroxide and a physical blend of calcium stearate and calcium hydroxide.

TABLE 5 pH Measurements

| Sample | n | pH |
|---|---|---|
| neutral calcium stearate | 0 | 7 |
| slightly basic calcium stearate | 0.3 | 9 |
| highly basic calcium stearate | 3 | 12 |
| $Ca(OH)_2$ | — | 14 |
| $Ca(OH)_2$ and $Ca(St)_2$ blend | — | 14 |

The above pH data may explain the superior performance of the calcium stearate composition of n=3 when compared to compositions having n=0 and n=0.3 in PVC. The physical blends of $Ca(St)_2$ and $Ca(OH)_2$ are highly basic (pH 14) which can promote dehydrochlorination in PVC. Neutral calcium stearate (n=0) and slightly basic calcium stearate (n=0.3) are less basic (pH 7, pH 9) and their ability to capture released HCl during processing is less effective, but they will not promote dehydrochlorination. By contrast, highly basic calcium stearate (n=3) has pH 12 which may be an optimum pH to capture released HCl, without promoting dehydrochlorination. Compositions of n greater than 3 will likewise have higher pH and may promote dehydrochlorination in PVC. Further, the lower pH for the highly basic calcium stearate (n=3) than for the physical blend of calcium stearate and calcium hydroxide illustrates that the excess calcium hydroxide in the highly basic calcium stearate (n=3) is not free to equilibrate with the aqueous phase, and is thus dispersed in the calcium stearate. As is shown for the calcium hydroxide and for the physical blend of calcium stearate and calcium hydroxide, it would be expected that the pH of the aqueous phase of a dispersion of the solids is about 14. By contrast, as is shown for the n=3 material, the pH of the aqueous phase of a dispersion of said composition in water is less than 14, indicating that the calcium hydroxide is not free to associate with the water and is otherwise bound with the calcium stearate.

EXAMPLE 18

Sample Morphology by Light Microscopy

Samples of neutral (n=0), slightly basic (n=0.3), and highly basic (n=3) calcium stearate compositions were viewed on a light microscope at 105×magnification using substage light only. The neutral calcium stearate composition transmitted more light than slightly basic stearate composition. The highly basic composition transmitted the least amount of light. It may be that stearic acid will transmit maximum light and $Ca(OH)_2$ transmits least amount of light. If one formulates higher ratios of $Ca(OH)_2$ to $Ca(St)_2$, then the degree of intimate mixing of $Ca(OH)_2$ into $Ca(St)_2$ will not be complete, thereby the excess $Ca(OH)_2$ will act as a free base to promote dehydrochlorination.

EXAMPLE 19

Tribasic Calcium Stearate 317.5 Kg of calcium hydroxide was charged to a Littleford mixer, followed by addition of 11.3 Kg of water. 606.9 Kg of melted stearic acid was then added with high intensity mixing. Total batch time was 30 minutes with reaction time of approximately 15 to 20 minutes. The analysis of the product showed an ash content of 26.95 percent.

EXAMPLE 20

Tribasic Calcium Stearate Modified with Zinc Stearate

Zinc stearate modified tribasic calcium stearate was prepared following the procedure of Example 19, modified only by the addition of 108.8 Kg of zinc stearate with the calcium hydroxide. The final product was 15 percent by weight zinc stearate on a dry basis. The analysis of the product showed an ash content of 25.13 percent.

EXAMPLE 21

Effect of Zinc Modified Compositions on PVC Stability

Figure 6:
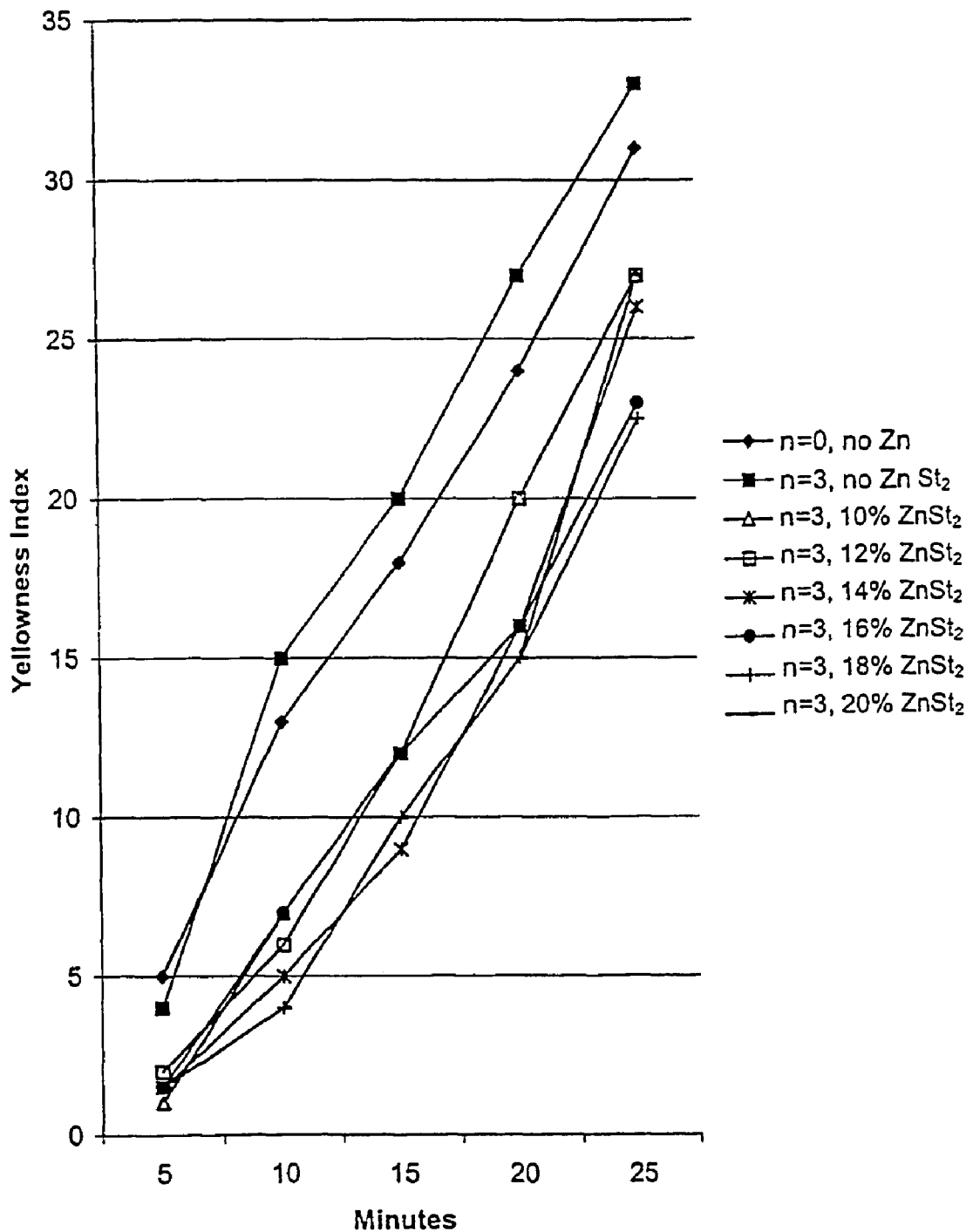
FIGS. 6-8 are graphs of Yellowness Index over time showing the effect of zinc on PVC stability over time.
Figure 7:
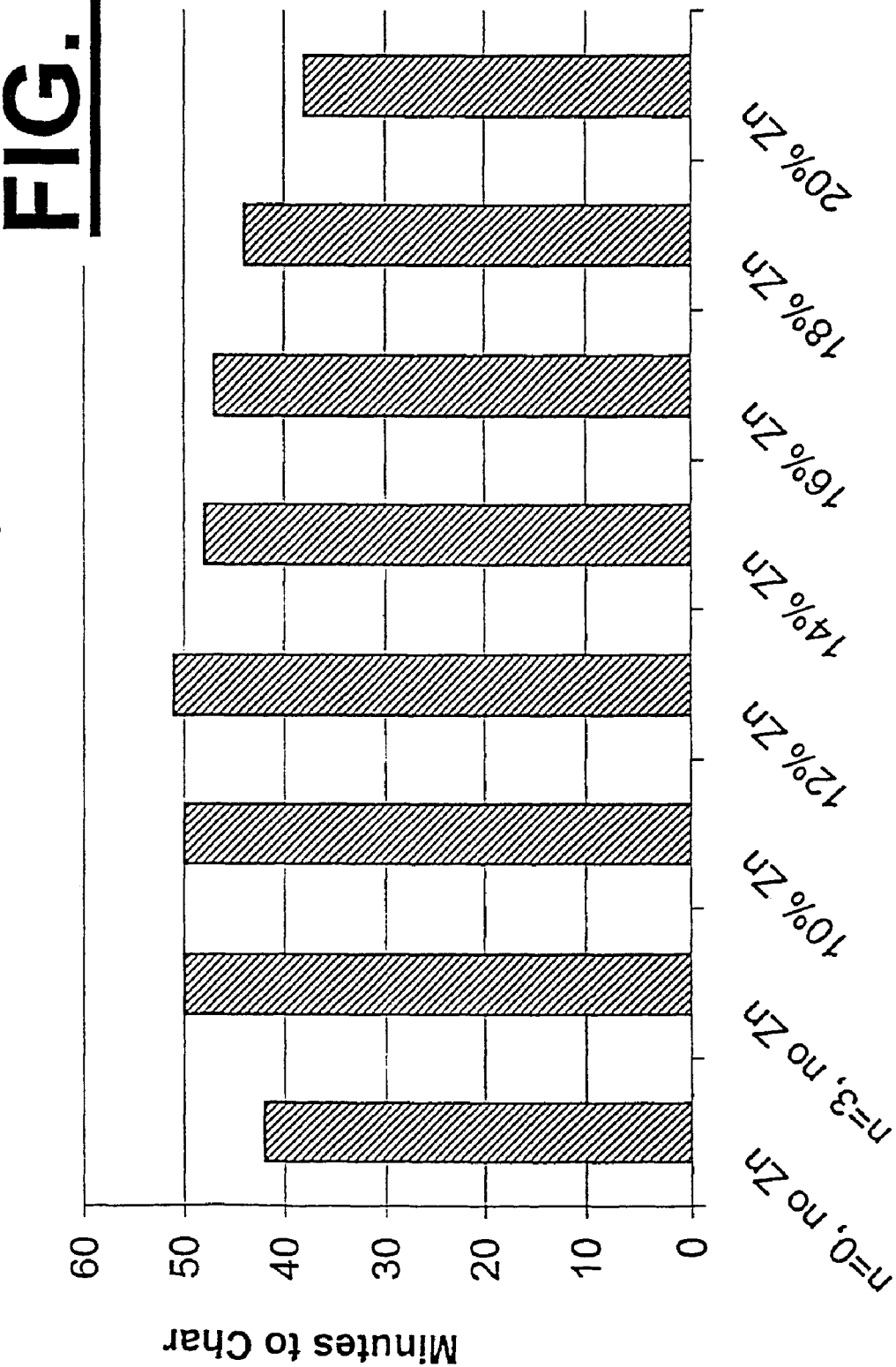
Figure 8:
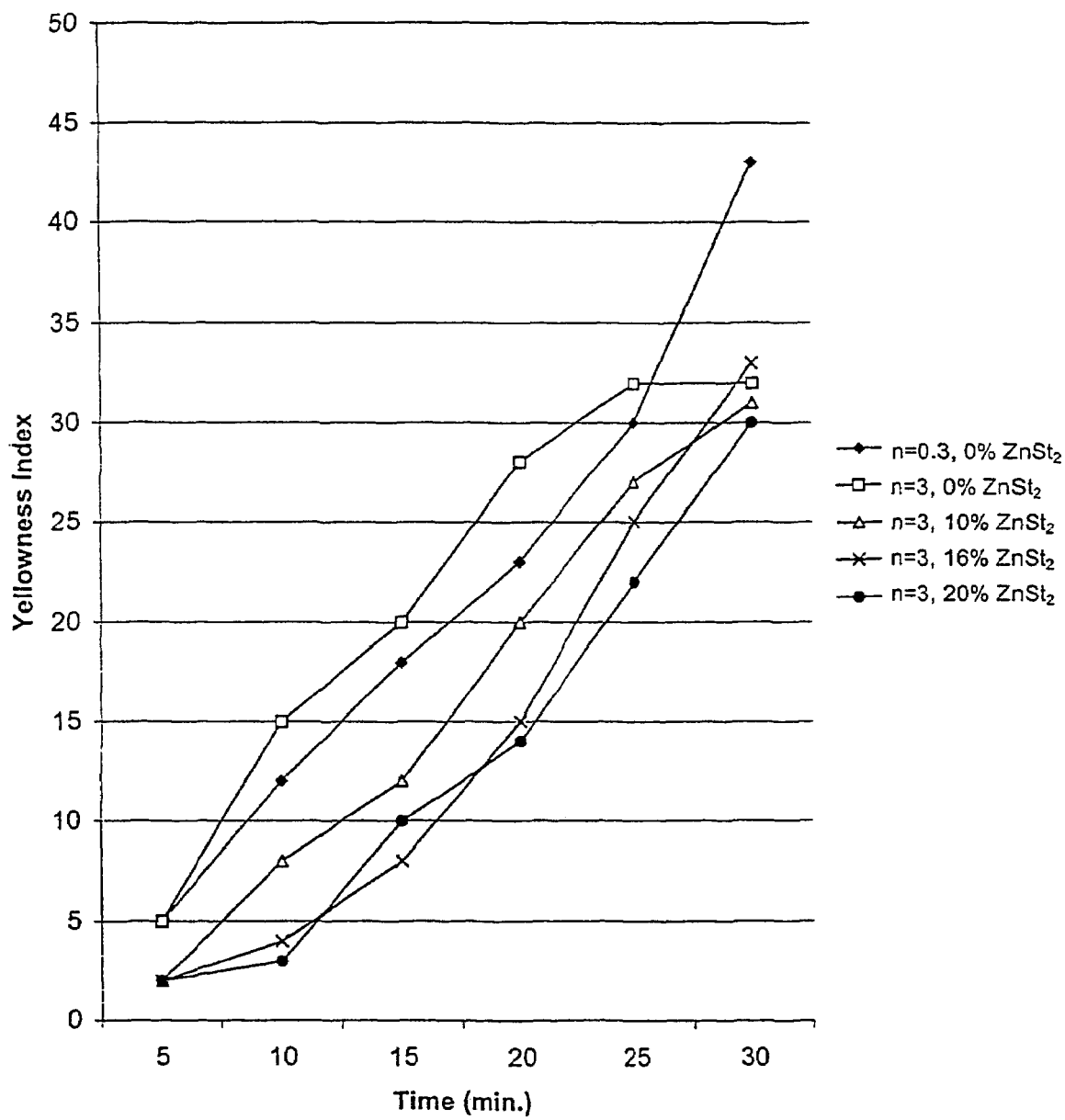

Zinc stearate modified tribasic calcium stearate compositions were prepared following the procedures of Example 20. These compositions were then evaluated for their ability to stabilize PVC as measured by Yellowness Index, following the procedures of Example 13. Results for various zinc stearate modified calcium stearate compositions are shown in FIGS. 6-8 where the level of added Zn stearate ranged from 10-20%. The addition of Zn has a positive beneficial effect on the ability to stabilize PVC compositions.

EXAMPLE 22

Moisture Uptake

Samples of tribasic calcium stearate composition (n=3) and a physical blend of calcium stearate and calcium hydroxide were evaluated for their ability to absorb water from air. The physical blend included 300 grams of neutral calcium stearate (n=0) mixed with 100 grams of calcium hydroxide. Samples of the physical blend and the tribasic material were exposed to humid air in a humidity chamber at 43° C. and the moisture uptake measured as shown in Table 6.

TABLE 6

Moisture Uptake

| Sample | Exposure Time, hrs | % weight gain |
|---|---|---|
| blend | 15 | 0.3 |
| n = 3 | 15 | 0.28 |
| blend | 24 | 0.5 |
| n = 3 | 24 | 0.3 |

TABLE 6-continued

Moisture Uptake

| Sample | Exposure Time, hrs | % weight gain |
|---|---|---|
| blend | 39 | 0.72 |
| n = 3 | 39 | 0.42 |

EXAMPLE 23

Carbon Dioxide Uptake

Samples as in Example 22 were evaluated for their ability to absorb carbon dioxide. The samples were held under 20 psi $CO_2$ pad bubbling 1 liter/min $CO_2$ through the system for 1 hour. A 400 gram sample of tribasic calcium stearate composition was similarly treated. Samples were then measured for weight gain as shown in Table 7.

TABLE 7

$CO_2$ Uptake

| Sample | Weight gain, grams |
|---|---|
| blend | 21.67 |
| n = 3 | 15.43 |

EXAMPLE 24

DSC of Calcium Stearate Compositions

Differential scanning calorimetry (DSC) was performed on three samples: calcium stearate composition with n=0.3, calcium stearate composition with n=3, and a physical blend of calcium stearate and calcium hydroxide as defined in Examples 22 and 23. A DSC trace for n=0.3 is shown in FIG. 9; a DSC trace for n=3 is shown in FIG. 10; a DSC trace for the physical blend is shown in FIG. 11.

Figure 9:
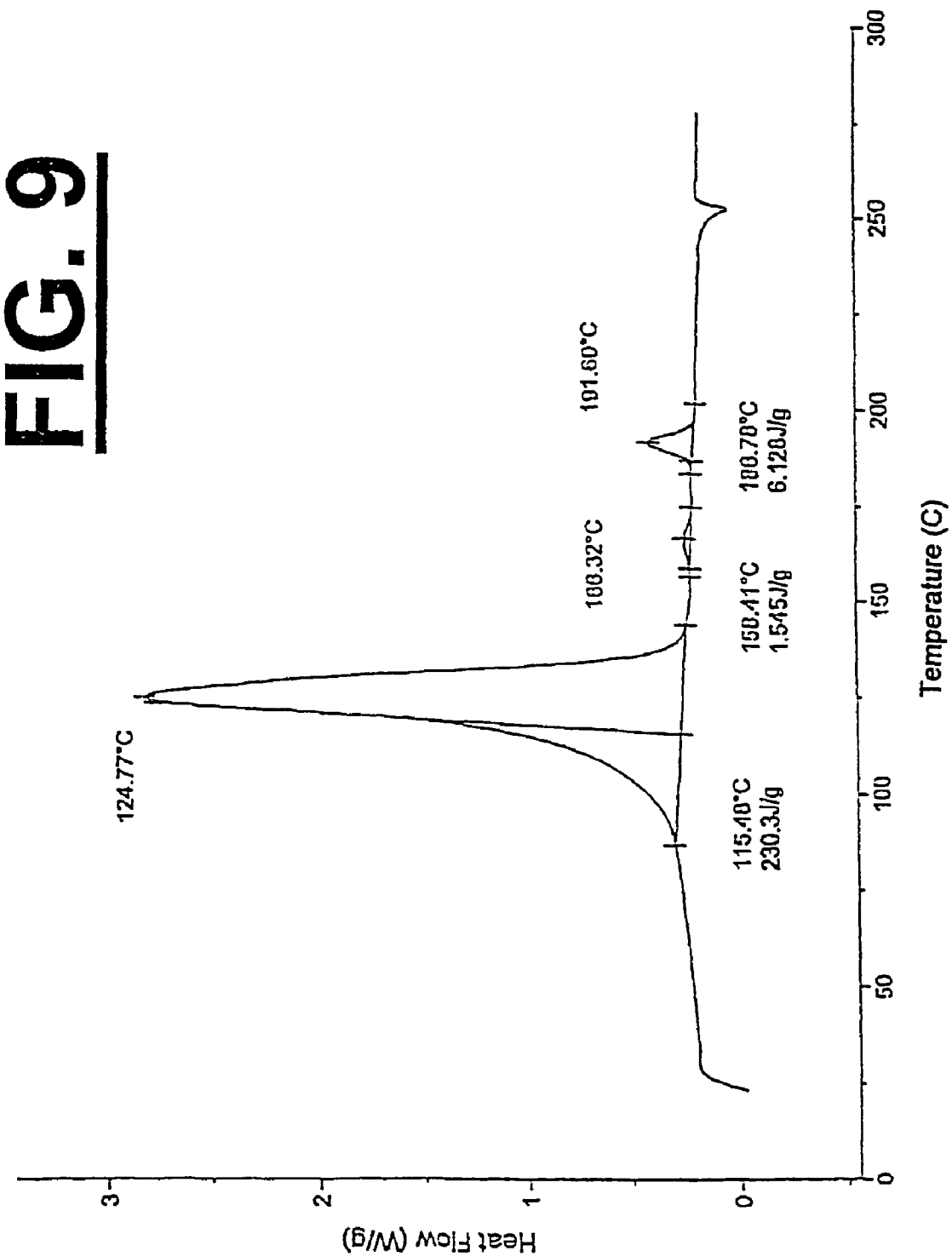
FIGS. 9-11 are differential scanning calorimetry traces for calcium stearate and calcium hydroxide having a molar excess of calcium hydroxide equivalent to n=0.3, 3 and a physical blend respectively.
Figure 10:
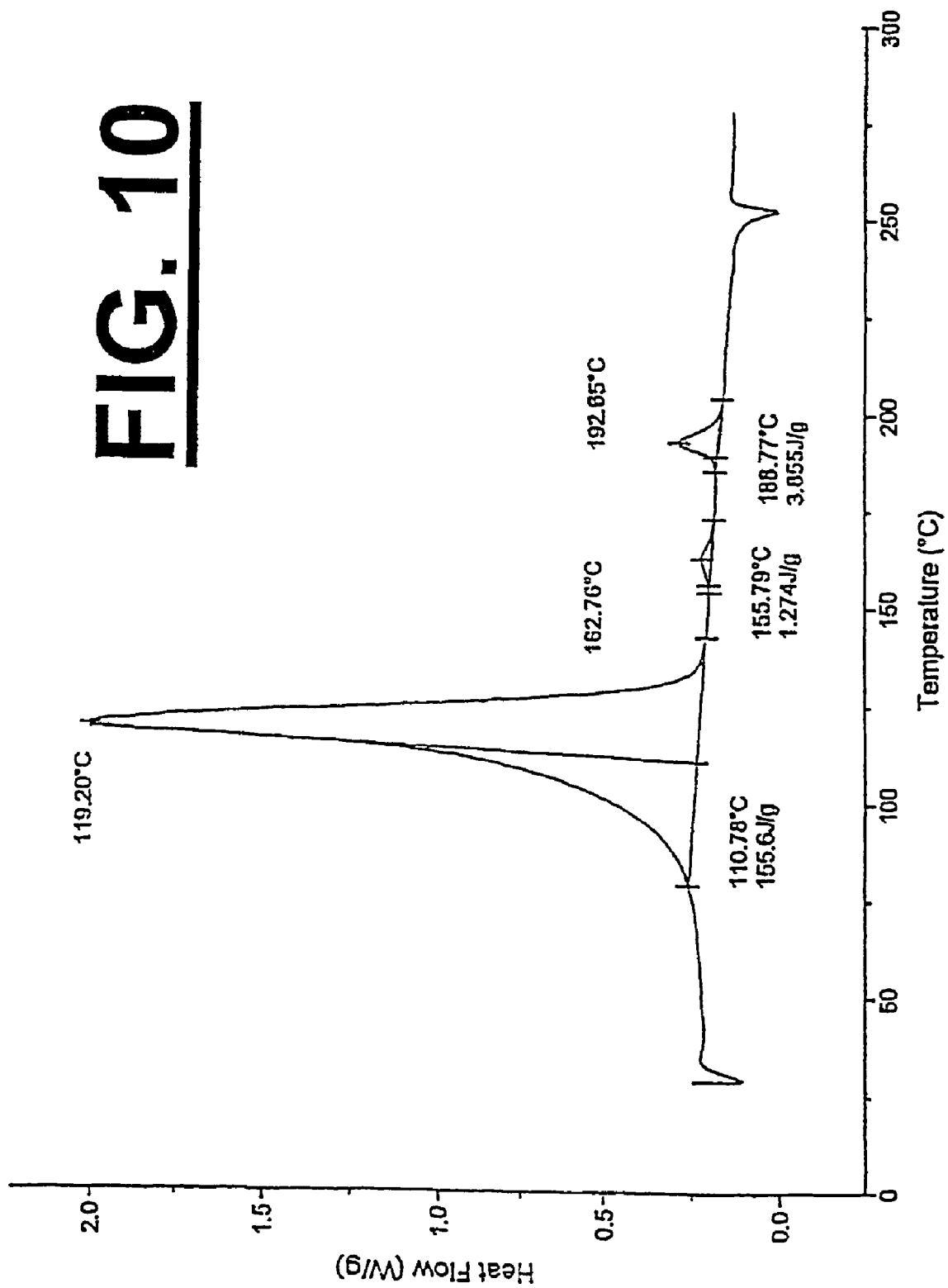
Figure 11:
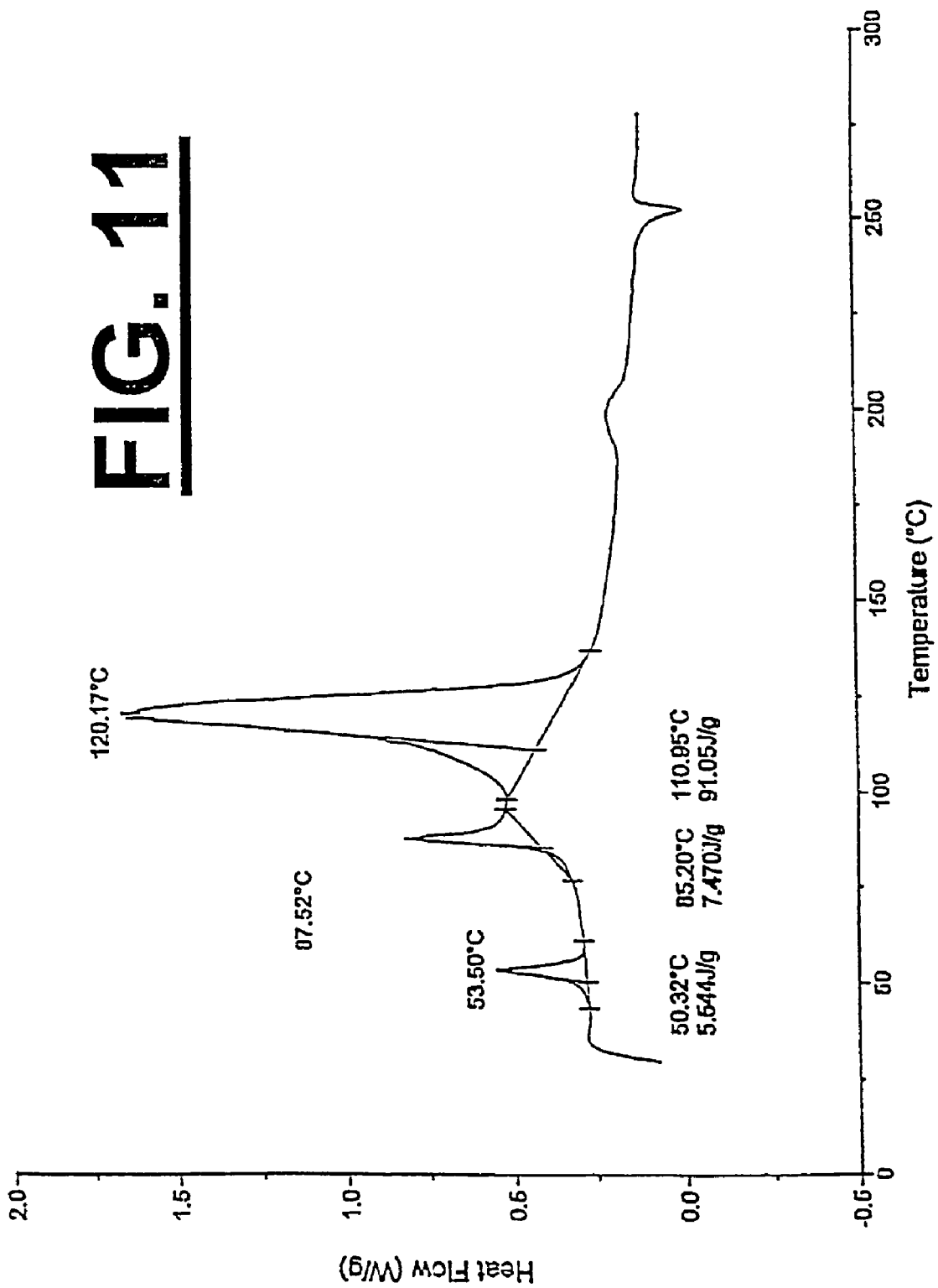

As can be seen from a comparison of FIGS. 9-11, calcium stearate compositions of the present invention exhibit peaks not seen for the physical blend. These peaks may indicate one or more thermal transitions characteristic of the calcium stearate compositions that is not seen in a physical blend of calcium stearate and calcium hydroxide. The calcium carboxylate compositions of the present invention may thus exhibit thermal transitions not seen in blends of calcium stearate and calcium hydroxide; in one embodiment these thermal transitions may occur at about 160 to 170° C. and at about 190 to 195° C. as illustrated in FIGS. 9 and 10.

EXAMPLE 25

FTIR of Calcium Stearate Compositions

FTIR scans of several samples were performed as shown in FIGS. 12A-D. FIG. 12A shows an FTIR spectrum of a powder calcium stearate composition of n=3. FIG. 12B shows and FTIR spectrum of a powder sample of a physical blend of neutral calcium stearate and calcium hydroxide having a molar excess of calcium hydroxide equivalent to n=3. FIG. 12C shows and FTIR spectrum of a melt calcium stearate composition of n=3. FIG. 12D shows an FTIR spectrum of a melt physical blend of neutral calcium stearate and calcium hydroxide.

Results and Discussion

FIGS. 1 and 2 compare the performance of slightly basic and two highly basic calcium stearates (n=0.3 and n=3 modified with 15% zinc stearate (n=0.3), respectively) when used with varying levels of organotin mercaptides from 0.5 to 1.75 phr in typical rigid PVC extrusion compounds. The data from the dynamic testing shown in these Figures illustrates how effective these highly basic stearates can be. In nearly all cases a 25% increase in long-term heat stability was observed when high ash calcium stearates were used. For example in FIG. 2 with organotin levels as low as 0.5 phr the standard product (n=0.3) offers a very narrow processing window whereas in the same formulation substituting only the calcium stearate (n=3, both unmodified and modified with 15% zinc stearate) the processing window can easily be doubled before polymer degradation occurs.

In most rigid PVC applications color retention is a major issue. It has been shown that high ash calcium stearates can produce equal or better color retention at 50% organotin stabilizer levels when comparing to the standard product. FIG. 1 clearly demonstrates this where sample 12g is the standard slightly basic calcium stearate at 1.0 phr organotin stabilizer and sample 12b is the highly basic calcium stearate at only 0.5 phr tin stabilizer. The early color hold and long-term heat stability are both superior to the standard, when using n=3 (modified with zinc stearate (12c) and unmodified (12b)) even at half the primary heat stabilizer loading.

FIG. 3 shows the general trend in color retention when replacing the standard calcium stearate with the high ash product. This trend is reproducible at nearly any organotin loading level. The yellowness index remains low and the L value, or whiteness, remains higher with the more basic stearates. That is to say, the time at which thermal decomposition occurs is extended in every case we have observed when compared to standard products.

In addition to the dynamic testing of PVC some static heat tests were also performed to see how the products held up. FIG. 5 shows the results of this testing. Samples compounded with the highly basic calcium stearates had markedly better early color and also better color retention when exposed to intense static heat. All results clearly demonstrate the marked superiority of the highly basic grades of calcium stearate in dynamic Brabender tests, FIGS. 1 and 2. Initial color and colors after accelerated QUV exposure FIG. 4, are also better for the highly basic grades of calcium stearate. Table 4 shows that when using highly basic stearates the physical properties of the polymer are equal to or better than the results for the standard calcium stearate. No disadvantages of using highly basic calcium stearates in rigid PVC formulations have been observed.

Highly basic calcium stearates are superior to neutral or slightly basic grades of calcium stearate and allow for lower use levels of organotin based heat stabilizers. They offer overall improved economics and weathering performance while retaining processing characteristics and physical properties of the rigid vinyl compounds.

In most countries of the world, lead-based stabilizer systems are still employed in rigid PVC applications for economic reasons. We believe that the improved synergistic effects of highly basic calcium stearates with low levels of organotin stabilizers will allow for the cost effective replacement of lead-based stabilizers with the more environmentally acceptable organotin primary stabilizers.

The compositions of the present invention provide surprising and unexpectedly superior performance as PVC additives as compared with calcium stearate alone or as a simple blend of calcium stearate and lime in the form of calcium hydroxide or calcium oxide. As is apparent from the above tables, the compositions of the present invention show unexpectedly superior ability to provide heat stability to PVC during extrusion, with the highly unexpected result that an optimum amount of excess calcium hydroxide of about n=3 results in a maximum heat stability.

Without wishing to be bound by any particular theory, one alternative reason for the observed ability of the compositions of the present invention to provide improved heat stability may reside in that the composition may comprise lime encapsulated calcium stearate particles with lime rich surfaces which render the calcium stearate buffered against the attack of strong acids such as HCl from PVC. The lime rich surfaces would also explain the resistance to plate out, the dissipation of static charge and the reduced dust explosivity. Alternatively, the calcium stearate may comprise a porous structure with small calcium hydroxide particles interspersed or intercalated in the pores. In this form, the excess calcium hydroxide may act as an acid scavenger protecting the calcium stearate from attack by hydrogen chloride released during extrusion of PVC.

The ability of the compositions of the present invention to provide superior heat stability to PVC is surprising and highly unexpected. Usually, the presence of excess calcium hydroxide in undesirable, as it may actually act as a catalyst for dehydrochlorination of PVC during extrusion, with the released HCl acting to reduce the heat stability of the PVC. This is the observed behavior in the heat stability results from the dry blended calcium stearate and calcium hydroxide of Example 9, wherein the heat stability of 15 minutes is inferior to the 17 minutes observed for stoichiometrically prepared calcium stearate in Example 5. However, when excess calcium hydroxide is thoroughly and intensively mixed with stearic acid or calcium stearate using the methods of the present invention, the resulting compositions show marked improvement in the ability to provide heat stability to PVC during extrusion. Even more unexpectedly, the ability of the compositions to affect heat stability appears to reach a maximum with an optimum excess of calcium hydroxide of about three moles, or n equal about 3. This is reflected in the observed heat stabilities of 21 minutes for n=0.3 as Example 12p, and an observed heat stability of 25 minutes for n=3. Again, while not wishing to be bound by any particular theory, it is possible that for excess calcium hydroxide below the optimum amount, the amount of interspersed or intercalated calcium hydroxide is insufficient to completely protect the calcium stearate from attack by released HCl. For excess calcium hydroxide above the optimum amount, it is possible that too much calcium hydroxide is present and not all can be incorporated into the calcium stearate structure, and the unincorporated calcium hydroxide acts as a dehydrochlorination catalyst to promote HCl release from the PVC. The HCl released due to unincorporated calcium hydroxide at n greater than the optimum may tend to offset the ability of the incorporated, interspersed or intercalated calcium hydroxide to protect the calcium stearate, thus resulting in a lower than maximum heat stability.

It is well known in the PVC industry that the addition of low levels of non-alkaline earth metal soaps, such as Mg, Ca, Ba, that the long-term heat stability of the compound can be extended. This is to say that the long-term color is better and the time to polymer degradation is lengthened. Formulation and evaluation of the tribasic calcium stearate compositions have shown this to be the case. Consequently, the addition of low level transition metal soaps, such as Zn, Cd, the early color can be improved. The trade-off is that the transition metal soaps decrease the time to decomposition even at very low levels. Further extending the time to decomposition in the tribasic calcium stearate composition allows reformulation with small additions of transition metals to improve early color without affecting the time to decomposition. Mixed-metal soaps are known, but when added in conjunction with the calcium stearate compositions of the present invention this would truly be a novel composition. A mixed-metal system in conjunction with the calcium stearate compositions could give increased long-term heat stability and also outstanding early color, something that is not available previous materials. FIGS. 6-8 show the effect of the zinc stearate modified calcium stearate composition of the present invention on stability in PVC.

The compositions of the present invention may be used in combination with other typical processing additives used with PVC or other polymers such as polyolefins, phenolics, reinforced polyesters and rubber. These additives may include one or more primary and secondary antioxidants, including hindered alkyl phenols and phosphites.

Therefore, what has been shown specifically above is a carboxylate composition comprising the formula $$(A)_2M.nD(OH)_2.xH_2O$$

wherein:
A is an organic fatty acid and is selected from the group consisting of saturated $C_{12-24}$ carboxylic acids, unsaturated $C_{12-24}$ carboxylic acids, aromatic $C_{12-24}$ carboxylic acids, alicyclic $C_{12-24}$ carboxylic acids, polycarboxylic acid derivatives thereof, anhydride derivatives thereof and blends thereof, most preferably stearic acid or the stearate anion;
M is a divalent cation, preferably calcium;
n is a fractional or whole number from about 1 to about 10 inclusive, most preferably 3;
D is an alkali earth metal, preferably calcium; and
x is a fractional or whole number from about 0 to about 3 inclusive, preferably 2.

The above composition will optionally comprise the formula $$(A)_2M.nD(OH)_2.xH_2O.m(B)_2N$$

wherein:
A is as defined above;
B is selected from A;
N is a divalent cation other than M, most preferably zinc; and
m is a fractional or whole number from 0 to about 1 inclusive, preferably 0.25.

In a more preferred embodiment, the additive composition is a solid phase dispersion of $D(OH)_2$ (the hydroxide) in $(A)_2M$ (the metal carboxylate). While the preferred carboxylate anion is stearate, it is recognized that other carboxylate anions are envisioned within the scope of the invention, particularly, laurate, myristate, palmitate, stearate, arachidate, behenate, and lignocerate, oleate, linoleate, linolenate or mixtures thereof. It is recognized that polycarboxylic acids as well as anhydride derivatives thereof are useful in this invention. Most preferably, the hydroxide component, $(D(OH)_2)$ will not completely separate from the metal carboxylate moiety $((A)_2M)$ when the carboxylate composition is immersed in water. When the additive is formed by the methods described, the additive composition, when dispersed in water, the aqueous phase will have a pH which is less than 14 and greater than 7, more preferably less than 14 and greater than about 9, and most preferably, about 12. The composition is added to a halogenated polymer, especially PVC, in an amount of from about 0.5 to about 2 parts per hundred parts polymer. When used in this fashion, lower amounts of the primary organotin mercaptide can be significantly reduced with similar or better results.

What is claimed is:

1. A carboxylate composition comprising the formula $$(A)_2M.nD(OH)_2.xH_2O$$

wherein:
A is an organic fatty acid and is selected from the group consisting of saturated $C_{12-24}$ carboxylic acids, unsaturated $C_{12-24}$ carboxylic acids, aromatic $C_{12-24}$ carboxylic acids, alicyclic $C_{12-24}$ carboxylic acids, polycarboxylic acid derivatives thereof, anhydride derivatives thereof and blends thereof;
M is a divalent cation;
n is a fractional or whole number from about 1 to about 10 inclusive;
D is an alkali earth metal;
x is a fractional or whole number from about 0 to about 3 inclusive; and
wherein said $D(OH)_2$ is a solid phase dispersion in $(A)_2M$.

2. The composition of claim 1, wherein said carboxylate compound further comprises the formula $$(A)_2M.nD(OH)_2.xH_2O.m(B)_2N$$

wherein:
N is a divalent cation other than M;
B is selected from A; and
m is a fractional or whole number from 0 to about 1 inclusive.

3. The composition of claim 1 wherein
n is from about 2 to about 4 inclusive.

4. The composition of claim 3 wherein
n is about 3.

5. The composition of claim 2 wherein
m is about 0.25.

6. The composition of claim 1 wherein
A is selected from the group consisting of laurate, myristate, palmitate, stearate, arachidate, behenate, and lignocerate, oleate, linoleate, linolenate or mixtures thereof.

7. The composition of claim 1 wherein
$D(OH)_2$ does not completely separate from $(A)2M$ when said carboxylate composition is immersed in water.

8. The composition of claim 1, wherein
in a dispersion of said composition in water, the pH of the aqueous phase of said dispersion is less than about 14 and greater than about 7.

9. The composition of claim 8, wherein
in a dispersion of said composition in water, the pH of the aqueous phase of said dispersion is less than about 14 and greater than about 9.

10. The composition of claim 9, wherein
in a dispersion of said composition in water, the pH of the aqueous phase of said dispersion is about 12.

11. The composition of claim 1 wherein
A is an organic fatty acid and is selected from the group consisting of saturated $C_{12-24}$ carboxylic acids, unsaturated $C_{12-24}$ carboxylic acids and blends thereof;
M is Ca;
n is about 3;
D is Ca; and
x is about 2.

12. The composition of claim 2 wherein
A is an organic fatty acid and is selected from the group consisting of saturated $C_{12-24}$ carboxylic acids, unsaturated $C_{12-24}$ carboxylic acids and blends thereof;
B is selected from A;
M is Ca;
N is Zn;
n is about 3;
D is Ca;
x is about 2; and
m is about 0.25.

13. The composition of claim 11 wherein
A is a stearate.

14. The composition of claim 12 wherein
A is a stearate; and
B is a stearate.

15. The composition of claim 12 which further comprises:
a halogenated polymer.

16. The composition of claim 15 wherein
said halogenated polymer is selected from the group consisting of polyvinyl chloride, polyvinylidene chloride, chlorinated polyvinyl chloride, chlorinated polyolefins and blends thereof.

17. The composition of claim 16 wherein
said composition is present in said polymer from about 0.5 to about 2 parts per hundred parts polymer.

18. A method of making a calcium carboxylate composition comprising:
obtaining an amount of fatty carboxylic acid;
obtaining an amount of a calcium hydroxide, such that the molar ratio of calcium to carboxylic acid is from about 2:2 to about 11:2;
forming a first mixture of said amount of said calcium hydroxide in dry form, optionally, from about 0 to about 90 percent of said amount of carboxylic acid in dry form, and an amount of water which ranges from no added water to an amount which is about 1.5 moles of water per mole of carboxylic acid;
forming a second mixture of said first mixture and from about 100 to about 10 percent of said amount of carboxylic acid in molten form; and
mixing said second mixture at least until said second mixture exotherms.

19. The method of claim 18, wherein
said molar ratio of metal to carboxylic acid is from about 3:2 to about 5:2.

20. The method of claim 19, wherein
said molar ratio of metal to carboxylic acid is about 4:2.

21. The method of claim 18, wherein
about 50 percent of said amount of carboxylic acid in dry from is added to form said first mixture; and
about 50 percent of said amount of carboxylic acid in molten form is added to form said second mixture.

22. The method of claim 18, wherein
100 percent of said fatty carboxylic acid is added in molten form in said second mixture.

23. The method of claim 18, wherein
said fatty carboxylic acid is selected from the group consisting of lauric, myristic, palmitic, stearic, arachidic, behenic, lignoceric, oleic, linoleic, and linolenic acids or mixtures thereof.

24. The method of claim 18, wherein
said step of forming said first mixture further comprises adding zinc stearate such that the molar ratio of said zinc stearate to said fatty carboxylic acid is from about to about 0.5.

25. The method of claim 18, wherein
said step of forming said first mixture further comprises adding zinc stearate such that the molar ratio of said zinc stearate to said fatty carboxylic acid is about 0.125.

26. The method of claim 18, wherein
said second mixture exotherm to a temperature less than the boiling point of water.

27. A method of stabilizing vinyl polymers, comprising:
adding to a halogenated polymer a stabilizer composition comprising at least one carboxylate composition comprising the formula $$(A)_2M \cdot nD(OH)_2 \cdot xH_2O$$

wherein:
A is an organic fatty acid and is selected from the group consisting of saturated $C_{12-24}$ carboxylic acids, unsaturated $C_{12-24}$ carboxylic acids, aromatic $C_{12-24}$ carboxylic acids, alicyclic $C_{12-24}$ carboxylic acids, polycarboxylic acid derivatives thereof, anhydride derivatives thereof and blends thereof;
M is a divalent cation;
n is a fractional or whole number from about 1 to about 10 inclusive;
D is an alkali earth metal;
x is a fractional or whole number from about 0 to about 3 inclusive; and
wherein said $D(OH)_2$ is a solid phase dispersion in $(A)_2M$.

28. The method of claim 27, wherein said metal carboxylate compound further comprises the formula $$(A)_2M \cdot nD(OH)_2 \cdot xH_2O \cdot m(B)_2N$$

wherein:
N is a divalent cation other than M;
B is selected from A; and
m is a fractional or whole number from 0 to about 1 inclusive.

29. The method of claim 27 wherein
n is from about 2 to about 4 inclusive.

30. The method of claim 29 wherein
n is about 3.

31. The method of claim 28 wherein
m is about 0.25.

32. The method of claim 27 wherein
A is selected from the group consisting of laurate, myristate, palmitate, stearate, arachidate, behenate, and lignocerate, oleate, linoleate, linolenate or mixtures thereof.

33. The method of claim 27 wherein
$D(OH)_2$ does not completely separate from $(A)_2M$ when said carboxylate composition is immersed in water.

34. The method of claim 27, wherein
in a dispersion of said composition in water, the pH of the aqueous phase of said dispersion is less than about 14 and greater than about 7.

35. The method of claim 34, wherein
in a dispersion of said composition in water, the pH of the aqueous phase of said dispersion is less than about 14 and greater than about 9.

36. The method of claim 35, wherein
in a dispersion of said composition in water, the pH of the aqueous phase of said dispersion is about 12.

37. The method of claim 27 wherein
A is an organic fatty acid and is selected from the group consisting of saturated $C_{12-24}$ carboxylic acids, unsaturated $C_{12-24}$ carboxylic acids and blends thereof;
M is Ca;
n is about 3;
D is Ca; and
x is about 2.

38. The method of claim 28 wherein
A is an organic fatty acid and is selected from the group consisting of saturated $C_{12-24}$ carboxylic acids, unsaturated $C_{12-24}$ carboxylic acids and blends thereof;
B is selected from A;
M is Ca;
N is Zn;
n is about 3;
D is Ca;
x is about 2; and
m is about 0.25.

39. The method of claim 37 wherein
A is a stearate.

40. The method of claim 38 wherein
A is a stearate; and
B is a stearate.

41. The method of claim 37 which further comprises:
the step of adding said composition to a halogenated polymer.

42. The method of claim 41 wherein
said halogenated polymer is selected from the group consisting of polyvinyl chloride, polyvinylidene chloride, chlorinated polyvinyl chloride, chlorinated polyolefins and blends thereof.

43. The method of claim 41 wherein
said composition is present in said polymer from about 0.5 to about 2 parts per hundred parts polymer.

44. The method of claim 38 which further comprises:
a halogenated polymer.

45. The method of claim 44 wherein
said halogenated polymer is selected from the group consisting of polyvinyl chloride, polyvinylidene chloride, chlorinated polyvinyl chloride, chlorinated polyolefins and blends thereof.

46. The method of claim 45 wherein
said composition is present in said polymer from about 0.5 to about 2 parts per hundred parts polymer.

* * * * *

UNITED STATES PATENT AND TRADEMARK OFFICE
CERTIFICATE OF CORRECTION

| | | |
|---|---|---|
| PATENT NO. | : 7,595,412 B2 | Page 1 of 1 |
| APPLICATION NO. | : 10/486769 | |
| DATED | : September 29, 2009 | |
| INVENTOR(S) | : Jennings et al. | |

It is certified that error appears in the above-identified patent and that said Letters Patent is hereby corrected as shown below:

On the Title Pg Item (75)

Ssatyan Kodali should be "Satyan Kodali"

Signed and Sealed this

Second Day of February, 2010

David J. Kappos
*Director of the United States Patent and Trademark Office*

UNITED STATES PATENT AND TRADEMARK OFFICE
CERTIFICATE OF CORRECTION

PATENT NO.      : 7,595,412 B2                                    Page 1 of 1
APPLICATION NO. : 10/486769
DATED           : September 29, 2009
INVENTOR(S)     : Jennings et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1137 days.

Signed and Sealed this

Twenty-eighth Day of September, 2010

David J. Kappos
*Director of the United States Patent and Trademark Office*